US008008437B2

(12) United States Patent
Ohara et al.

(10) Patent No.: US 8,008,437 B2

(45) Date of Patent: Aug. 30, 2011

(54) CANCER-ASSOCIATED GENES

(75) Inventors: Osamu Ohara, Chiba (JP); Takahiro Nagase, Chiba (JP); Daisuke Nakajima, Chiba (JP); Shin-ichi Funahashi, Ibaraki (JP)

(73) Assignees: Kazusa DNA Research Institute Foundation, Kisarazu-shi (JP); Chugai Seiyaku Kabushiki Kaisha, Tokyo (JP)

( * ) Notice: Subject to any disclaimer, the term of this patent is extended or adjusted under 35 U.S.C. 154(b) by 565 days.

(21) Appl. No.: 12/099,513

(22) Filed: Apr. 8, 2008

(65) Prior Publication Data

US 2008/0262202 A1 Oct. 23, 2008

Related U.S. Application Data

(62) Division of application No. 10/451,000, filed as application No. PCT/JP01/11305 on Dec. 21, 2001, now Pat. No. 7,375,199.

(30) Foreign Application Priority Data

Dec. 22, 2000 (JP) ................................ 2000-389742

(51) Int. Cl.
*C07K 5/00* (2006.01)

(52) U.S. Cl. ...................................................... 530/350

(58) Field of Classification Search ........................ None
See application file for complete search history.

(56) References Cited

U.S. PATENT DOCUMENTS

2004/0048282 A1 3/2004 Smolyar

FOREIGN PATENT DOCUMENTS

| | | | |
|---|---|---|---|
| JP | 8-107797 | A | 4/1996 |
| WO | WO-93/16178 | A2 | 8/1993 |
| WO | WO9316178 | * | 8/1993 |
| WO | WO-98/55643 | A1 | 12/1998 |
| WO | WO-00/52044 | A1 | 9/2000 |
| WO | WO0246403 | * | 6/2002 |
| WO | WO-02/068579 | A2 | 9/2002 |

OTHER PUBLICATIONS

Nagase et al , DNA Research 7: 347-355, Dec. 31, 2000.*
Sequence search result (Nagase) 2010.*
Sequence search result,( Smolyar, protein and DNA) 2010.*
Sequence search result (Venter). 2010.*
Current Protocols in Protein science (1995, Science-section 5.1, published 1995.*
Sorthern blot hybridization protocol, 2000.*
Auffray, Charles, et al. Image: integration au niveau moleculaire de lanalyse du genome humain et de son expression, C.R. Acad. Sci. III, 1995, vol. 318, No. 2, pp. 263-272.
Aurrfray, Charles, et al. partial cDNA seuence, Fasta, Sep. 30, 1995, Accession Z44922.
Database EMBL 'Online! Homo sapiens chromosome 15 clone RP11-64K12, retrieved from EBI Database accession No. ACO 13356-XP-002277568—Abstract (Apr. 27, 2001).
Nagase et al., DNA Research, Universal Academy Press, JP, vol. 7, No. 6, pp. 347-355, (Dec. 31, 2000)-XP-001068355.
Database EMBL 'Online! Homo sapiens mRNA for KIAA1742 partial cds, retrieved from EBI Database accession No. ABO51529-XP-002277577—Abstract, (May 12, 2002).
Uniprot database, accession No. Q8CB10, 1999.
Brennan FM, Chantry, D Jackson AM, Maini RN, Feldmann M. J Autoimmun. Jun. 1989, vol. 2 Suppl: 177-86.
Zimmer DB. Cell Motil Cytoskeleton. 1991; 20(4): 325-37.
Powell et al., Parmacogenetics, 1998, vol. 8, pp. 411-421.
Carrere J, Guy-Crotte O, Gaia E, Figarella C. Apr. 1999; 44(4): 545-51.
Guo GL, Choudhuri S, Klaassen Cd.J Pharmacol Exp Ther. Jan. 2002; 300(1):206-12.
Jang A and Hill RP. Clin Exp Metastasis. Sep. 1997; 15(5):469-83.
Hell et al., Laboratory Investigation, 1995, vol. 73, pp. 492-4946.
Walker et al., Genome Research, vol. 9, No. 12, pp. 1198-1203, (Dec. 1999)-XP 000872154.
Hillier, L., et al. yf97b01. r1 Soars infant brain 1N1B Homo sapiens CDNA clone, Fasta, Apr. 14, 1995, Accession R18623.

* cited by examiner

*Primary Examiner* — Misook Yu
*Assistant Examiner* — Lei Yao
(74) *Attorney, Agent, or Firm* — Birch, Stewart, Kolasch & Birch, LLP.

(57) ABSTRACT

The present invention is related to a DNA comprising a nucleotide sequence encoding a polypeptide represented by SEQ ID NO:1 or SEQ ID NO:2. The DNA according to the present invention is highly expressed in prostatic adenocarcinoma and ovarian carcinoma, and is a cancer-associated gene, so that it is possible to inhibit cancer by blocking the binding of the present protein to its ligand. Accordingly, the present antibody is used not only in the detection of the present protein, but also as an agent for the treatment or prevention of cancers such as prostatic adenocarcinoma and ovarian carcinoma.

5 Claims, 1 Drawing Sheet

SEQUENCE LISTING

```
<160> NUMBER OF SEQ ID NOS: 21

<210> SEQ ID NO 1
<211> LENGTH: 5035
<212> TYPE: DNA
<213> ORGANISM: Homo sapiens
<220> FEATURE:
<221> NAME/KEY: CDS
<222> LOCATION: (561)..(4295)

<400> SEQUENCE: 1

ctcgccgccg ctgccgccgc caccgccgcc gccgccgccg ccgccgccgc ggcttcagca      60

ccagcgcccg gacagcggtg ccgcccacgg gcatggacgg tgacagcagc agcagcagcg     120

gcggcagcgg tccggctccc ggcccgggtc cggaagggga gcaacggccc gagggggagc     180

ccttggcccc agacggcggc tccccggaca gcacccagac caaggctgtg gcccctgagg     240

caagcccaga gagaagctcc tccctccaca gctgccccct ggaggaccct ttcagctctt     300

taggaccccc accaacaact ttcaccctcc agcctgtggg tccatccagc cccttggccc     360
```

```
ctgcccactt tacctatacc cgggcactgt aggaatacca ggggggcagt tccctgccag    420

gacttgggga tcgggcagct ctctgctccc acggctccag cctcagccct tctccagccc    480

cctcacagcg cgatgggacc tggaagccac ccgctgtgca gcaccatgtg gtcagcgtca    540

ggcaggaacg agccttccag atg cca aag agc tat tcc cag ctg att gct gag    593
                      Met Pro Lys Ser Tyr Ser Gln Leu Ile Ala Glu
                      1               5                   10

tgg cca gtg gcc gtg ctg atg ctg tgt ctg gct gtc atc ttc ctc tgc      641
Trp Pro Val Ala Val Leu Met Leu Cys Leu Ala Val Ile Phe Leu Cys
            15                  20                  25

acc ctg gct gga ctg ttg ggg gcc cgg ctg ccc gac ttc tcc aag cct      689
Thr Leu Ala Gly Leu Leu Gly Ala Arg Leu Pro Asp Phe Ser Lys Pro
        30                  35                  40

ttg ctg ggc ttt gag cca cgg gac aca gac att ggg agc aag tta gtg      737
Leu Leu Gly Phe Glu Pro Arg Asp Thr Asp Ile Gly Ser Lys Leu Val
    45                  50                  55

gtc tgg aga gca cta caa gcc ctc aca ggc ccc agg aag ctg ctt ttc      785
Val Trp Arg Ala Leu Gln Ala Leu Thr Gly Pro Arg Lys Leu Leu Phe
60                  65                  70                  75

ctt tcc cca gac ctt gag ctg aac agc tcg agc tcc cac aac act ctg      833
Leu Ser Pro Asp Leu Glu Leu Asn Ser Ser Ser Ser His Asn Thr Leu
                80                  85                  90

agg cct gca ccc aga ggc agt gcc cag gag agc gct gtc cgg cct cgg      881
Arg Pro Ala Pro Arg Gly Ser Ala Gln Glu Ser Ala Val Arg Pro Arg
            95                  100                 105

aga atg gtg gag ccc ctg gag gac aga agg caa gag aac ttc ttc tgt      929
Arg Met Val Glu Pro Leu Glu Asp Arg Arg Gln Glu Asn Phe Phe Cys
        110                 115                 120

ggc ccc cct gag aag agc tat gca aag ctg gtg ttc atg tcc acc tcc      977
Gly Pro Pro Glu Lys Ser Tyr Ala Lys Leu Val Phe Met Ser Thr Ser
    125                 130                 135

tcg ggc agc cta tgg aac ctg cat gcc atc cat tcc atg tgt cgc atg     1025
Ser Gly Ser Leu Trp Asn Leu His Ala Ile His Ser Met Cys Arg Met
140                 145                 150                 155

gaa cag gac cag atc cgc tcc cat acc agc ttc ggg gct ctg tgc cag     1073
Glu Gln Asp Gln Ile Arg Ser His Thr Ser Phe Gly Ala Leu Cys Gln
                160                 165                 170

cgg aca gca gcc aac cag tgc tgc ccc agc tgg tcc ctg ggc aac tat     1121
Arg Thr Ala Ala Asn Gln Cys Cys Pro Ser Trp Ser Leu Gly Asn Tyr
            175                 180                 185

ctg gct gtg ctc tcc aac cgc tcc tcc tgc ctg gac act acc caa gct     1169
Leu Ala Val Leu Ser Asn Arg Ser Ser Cys Leu Asp Thr Thr Gln Ala
        190                 195                 200

gac gca gcc cgc aca ctg gcc ctg ctt cgg acc tgt gcc ctc tac tac     1217
Asp Ala Ala Arg Thr Leu Ala Leu Leu Arg Thr Cys Ala Leu Tyr Tyr
    205                 210                 215

cac agt ggc gcc ttg gtg ccc tct tgt ctg gga cct ggg cag aac aag     1265
His Ser Gly Ala Leu Val Pro Ser Cys Leu Gly Pro Gly Gln Asn Lys
220                 225                 230                 235

tcc cca cgc tgt gcc cag gtt ccc acc aag tgc tcc cag agt agt gcc     1313
Ser Pro Arg Cys Ala Gln Val Pro Thr Lys Cys Ser Gln Ser Ser Ala
                240                 245                 250

atc tac caa ctc ctg cac ttt ctg ctt gac agg gac ttt ctg agt ccc     1361
Ile Tyr Gln Leu Leu His Phe Leu Leu Asp Arg Asp Phe Leu Ser Pro
            255                 260                 265

cag acc act gac tac cag gtg cct tcc ctc aag tac agc ctg ctc ttc     1409
Gln Thr Thr Asp Tyr Gln Val Pro Ser Leu Lys Tyr Ser Leu Leu Phe
        270                 275                 280

ctg ccc acc cca aag ggt gct tcc ctc atg gac atc tac ctg gac cgg     1457
```

```
Leu Pro Thr Pro Lys Gly Ala Ser Leu Met Asp Ile Tyr Leu Asp Arg
    285                 290                 295

ctg gcc acc ccc tgg ggg ctt gct gac aac tac acc tct gtc act ggc      1505
Leu Ala Thr Pro Trp Gly Leu Ala Asp Asn Tyr Thr Ser Val Thr Gly
300                 305                 310                 315

atg gac ctg ggc ctc aag cag gag ctg ctg agg cac ttc ctg gtc cag      1553
Met Asp Leu Gly Leu Lys Gln Glu Leu Leu Arg His Phe Leu Val Gln
                320                 325                 330

gac acg gtg tac ccc ttg ctg gct ctg gtt gcc atc ttc ttc ggc atg      1601
Asp Thr Val Tyr Pro Leu Leu Ala Leu Val Ala Ile Phe Phe Gly Met
            335                 340                 345

gcc ctg tac ctg cgc tca ctc ttc ctc acg ctc atg gtg ctg ctg ggg      1649
Ala Leu Tyr Leu Arg Ser Leu Phe Leu Thr Leu Met Val Leu Leu Gly
        350                 355                 360

gtg ctg ggc tca ctg ctg gtg gcc ttc ttc ctt tac cag gtg gcc ttc      1697
Val Leu Gly Ser Leu Leu Val Ala Phe Phe Leu Tyr Gln Val Ala Phe
    365                 370                 375

cgc atg gcc tac ttc ccc ttc gtc aat ctg gca gcc ctc ctc ctg ctg      1745
Arg Met Ala Tyr Phe Pro Phe Val Asn Leu Ala Ala Leu Leu Leu Leu
380                 385                 390                 395

agc agc gtc tgc gcc aac cac acg ctc atc ttc ttc gac ctg tgg cgc      1793
Ser Ser Val Cys Ala Asn His Thr Leu Ile Phe Phe Asp Leu Trp Arg
                400                 405                 410

ctt agc aag agc cag ctg ccg tcg ggg ggg ctg gcg cag cgc gtg ggc      1841
Leu Ser Lys Ser Gln Leu Pro Ser Gly Gly Leu Ala Gln Arg Val Gly
            415                 420                 425

cgc acc atg cac cac ttc ggc tac ctg ctg ctg gtc tcc ggc ctc acc      1889
Arg Thr Met His His Phe Gly Tyr Leu Leu Leu Val Ser Gly Leu Thr
        430                 435                 440

acg agc gcg gcc ttc tat gcc agc tac ctg agc cgc ctg ccg gcc gtt      1937
Thr Ser Ala Ala Phe Tyr Ala Ser Tyr Leu Ser Arg Leu Pro Ala Val
    445                 450                 455

cgc tgc ctc gcc ctc ttc atg ggc acg gct gtg ctg gtg cac ctg gcg      1985
Arg Cys Leu Ala Leu Phe Met Gly Thr Ala Val Leu Val His Leu Ala
460                 465                 470                 475

ctc acg ctg gtc tgg ctg ccc gcc tcc gcc gtg ctc cac gag cgc tac      2033
Leu Thr Leu Val Trp Leu Pro Ala Ser Ala Val Leu His Glu Arg Tyr
                480                 485                 490

ctg gcg cgc ggc tgt gcg cgc cgg gcg cgg ggc cgg tgg gag ggc agc      2081
Leu Ala Arg Gly Cys Ala Arg Arg Ala Arg Gly Arg Trp Glu Gly Ser
            495                 500                 505

gcg ccc cgg cgg cta ctg ctg gcg ctg cac cgg cgg ctc cgc ggc ctg      2129
Ala Pro Arg Arg Leu Leu Leu Ala Leu His Arg Arg Leu Arg Gly Leu
        510                 515                 520

cgg agg gcg gcg gct ggc acc tcg cgt ctg ctc ttc cag cgc ctg ctg      2177
Arg Arg Ala Ala Ala Gly Thr Ser Arg Leu Leu Phe Gln Arg Leu Leu
    525                 530                 535

ccc tgc ggc gtc atc aag ttc cgc tac atc tgg atc tgc tgg ttc gca      2225
Pro Cys Gly Val Ile Lys Phe Arg Tyr Ile Trp Ile Cys Trp Phe Ala
540                 545                 550                 555

gca ctg gcg gca ggg ggc gcc tac atc gcc gga gtc agc ccc cgc ctg      2273
Ala Leu Ala Ala Gly Gly Ala Tyr Ile Ala Gly Val Ser Pro Arg Leu
                560                 565                 570

cgg ctg ccc acg ctg ccg ccg ccc ggc ggc cag gtc ttc cgg ccc agc      2321
Arg Leu Pro Thr Leu Pro Pro Pro Gly Gly Gln Val Phe Arg Pro Ser
            575                 580                 585

cac ccc ttc gag cgc ttc gac gca gag tat cgc cag ctg ttc ctg ttc      2369
His Pro Phe Glu Arg Phe Asp Ala Glu Tyr Arg Gln Leu Phe Leu Phe
        590                 595                 600

gag cag ctg ccg cag ggc gag ggc ggc cac atg ccc gtg gtt ttg gtg      2417
```

```
Glu Gln Leu Pro Gln Gly Glu Gly Gly His Met Pro Val Val Leu Val
    605                 610                 615

tgg ggc gtc ctg cct gtg gac act ggc gac cct ctg gac cct cgt agc      2465
Trp Gly Val Leu Pro Val Asp Thr Gly Asp Pro Leu Asp Pro Arg Ser
620                 625                 630                 635

aac agc agc ctg gtg agg gac cct gcc ttc tcg gcc agc ggc cct gag      2513
Asn Ser Ser Leu Val Arg Asp Pro Ala Phe Ser Ala Ser Gly Pro Glu
                640                 645                 650

gcc cag cgc tgg ctg ctg gca ctc tgt cac cgg gcc cgg aat cag agc      2561
Ala Gln Arg Trp Leu Leu Ala Leu Cys His Arg Ala Arg Asn Gln Ser
            655                 660                 665

ttc ttc gac acc ctg cag gaa ggc tgg ccc acg ctg tgt ttc gtg gag      2609
Phe Phe Asp Thr Leu Gln Glu Gly Trp Pro Thr Leu Cys Phe Val Glu
        670                 675                 680

acc ctc cag cgc tgg atg gag agc ccc agc tgc gcc cgc ctg ggg cct      2657
Thr Leu Gln Arg Trp Met Glu Ser Pro Ser Cys Ala Arg Leu Gly Pro
    685                 690                 695

gac ctc tgc tgc ggc cac tcg gac ttc ccc tgg gcc ccc cag ttt ttc      2705
Asp Leu Cys Cys Gly His Ser Asp Phe Pro Trp Ala Pro Gln Phe Phe
700                 705                 710                 715

ctg cac tgc ctg aaa atg atg gct ctg gag caa ggc ccc gat ggc acc      2753
Leu His Cys Leu Lys Met Met Ala Leu Glu Gln Gly Pro Asp Gly Thr
                720                 725                 730

cag gac ctg gga ctc cgc ttt gat gcc cat ggc agc ctg gcc gcc ctg      2801
Gln Asp Leu Gly Leu Arg Phe Asp Ala His Gly Ser Leu Ala Ala Leu
            735                 740                 745

gtc cta caa ttc cag acc aac ttc cgg aac agt ccg gac tac aac cag      2849
Val Leu Gln Phe Gln Thr Asn Phe Arg Asn Ser Pro Asp Tyr Asn Gln
        750                 755                 760

acc cag ctc ttc tac aat gag gtc agc cac tgg ctg gca gcg gag ctg      2897
Thr Gln Leu Phe Tyr Asn Glu Val Ser His Trp Leu Ala Ala Glu Leu
    765                 770                 775

ggc atg gca cct cca ggc ctc cgc cgt ggt tgg ttc act agc cgt cta      2945
Gly Met Ala Pro Pro Gly Leu Arg Arg Gly Trp Phe Thr Ser Arg Leu
780                 785                 790                 795

gag ctg tat agc ctg cag cac agc ctg agc act gag cct gct gtg gtg      2993
Glu Leu Tyr Ser Leu Gln His Ser Leu Ser Thr Glu Pro Ala Val Val
                800                 805                 810

ctg ggc ctg gct ttg gcg ctg gcc ttt gcc aca ctg ctc ctg ggc acc      3041
Leu Gly Leu Ala Leu Ala Leu Ala Phe Ala Thr Leu Leu Leu Gly Thr
            815                 820                 825

tgg aat gtt ccc ctc agc cta ttc tcc gtg gca gct gtg gca ggc acc      3089
Trp Asn Val Pro Leu Ser Leu Phe Ser Val Ala Ala Val Ala Gly Thr
        830                 835                 840

gtg ctg ctc act gta gga ctc ctg gtt ctc ctc gag tgg cag ctc aac      3137
Val Leu Leu Thr Val Gly Leu Leu Val Leu Leu Glu Trp Gln Leu Asn
    845                 850                 855

act gcc gag gcc ctg ttt ctc tct gcc tca gtg ggc ctc tca gta gac      3185
Thr Ala Glu Ala Leu Phe Leu Ser Ala Ser Val Gly Leu Ser Val Asp
860                 865                 870                 875

ttc act gtc aac tac tgc atc tcc tat cac ctg tgc cca cac cct gac      3233
Phe Thr Val Asn Tyr Cys Ile Ser Tyr His Leu Cys Pro His Pro Asp
                880                 885                 890

cgc ctg agc cgt gtg gcc ttc tct ctg cgc cag acc agc tgc gcc aca      3281
Arg Leu Ser Arg Val Ala Phe Ser Leu Arg Gln Thr Ser Cys Ala Thr
            895                 900                 905

gcc gtg ggg gct gca gcc ctg ttt gcg gca ggc gtg ctc atg ctg cct      3329
Ala Val Gly Ala Ala Ala Leu Phe Ala Ala Gly Val Leu Met Leu Pro
        910                 915                 920

gcc aca gtg ctg ctc tat cgc aag ctg ggc atc atc ctc atg atg gtc      3377
```

```
Ala Thr Val Leu Leu Tyr Arg Lys Leu Gly Ile Ile Leu Met Met Val
    925                 930                 935

aaa tgc gtc agt tgt ggc ttt gcc agc ttc ttc ttc caa tct ctc tgc     3425
Lys Cys Val Ser Cys Gly Phe Ala Ser Phe Phe Phe Gln Ser Leu Cys
940                 945                 950                 955

tgt ttc ttc ggg cca gag aag aac tgt ggg cag atc ctc tgg ccc tgt     3473
Cys Phe Phe Gly Pro Glu Lys Asn Cys Gly Gln Ile Leu Trp Pro Cys
                960                 965                 970

gcc cac ctg cca tgg gat gct ggt act ggg gac cct ggt ggg gag aag     3521
Ala His Leu Pro Trp Asp Ala Gly Thr Gly Asp Pro Gly Gly Glu Lys
            975                 980                 985

gca ggc cgc cca cga cca ggg tca gtg gga ggg atg ccc  ggg tcc tgc     3569
Ala Gly Arg Pro Arg Pro Gly Ser Val Gly Gly Met Pro  Gly Ser Cys
        990                 995                 1000

tca gag  caa tat gag cta cag  ccc ctg gca cgg cgt  cgg agc ccc     3614
Ser Glu  Gln Tyr Glu Leu Gln  Pro Leu Ala Arg Arg  Arg Ser Pro
    1005                 1010                 1015

agc ttt  gac acc agc aca gcc  acc agc aag ctg tcc  cac cgg ccc     3659
Ser Phe  Asp Thr Ser Thr Ala  Thr Ser Lys Leu Ser  His Arg Pro
    1020                 1025                 1030

tca gta  ctc tct gag gat ctg  cag ctc cat gat ggt  ccg tgc tgt     3704
Ser Val  Leu Ser Glu Asp Leu  Gln Leu His Asp Gly  Pro Cys Cys
    1035                 1040                 1045

tcc cgg  ccc cca cca gcc cct  gcc tcc cca agg gag  ctg ctg ctg     3749
Ser Arg  Pro Pro Pro Ala Pro  Ala Ser Pro Arg Glu  Leu Leu Leu
    1050                 1055                 1060

gac cac  cag gca gtc ttc agc  cag tgc cct gcc ctg  cag acc tcc     3794
Asp His  Gln Ala Val Phe Ser  Gln Cys Pro Ala Leu  Gln Thr Ser
    1065                 1070                 1075

tcc ccc  tat aag cag gct ggc  ccc agc ccc aaa acc  cgg gcc agg     3839
Ser Pro  Tyr Lys Gln Ala Gly  Pro Ser Pro Lys Thr  Arg Ala Arg
    1080                 1085                 1090

cag gac  tcc caa ggg gag gag  gct gag ccc ctg cca  gcc tca cca     3884
Gln Asp  Ser Gln Gly Glu Glu  Ala Glu Pro Leu Pro  Ala Ser Pro
    1095                 1100                 1105

gaa gcc  cca gcc cac tct cct  aag gcc aag gct gca  gat cct cct     3929
Glu Ala  Pro Ala His Ser Pro  Lys Ala Lys Ala Ala  Asp Pro Pro
    1110                 1115                 1120

gat ggc  ttc tgt tcc tca gcc  agc acc ctg gag ggg  ctc agc gtc     3974
Asp Gly  Phe Cys Ser Ser Ala  Ser Thr Leu Glu Gly  Leu Ser Val
    1125                 1130                 1135

tct gat  gag acc tgc cta agc  acc tct gag ccc agt  gcc cgt gta     4019
Ser Asp  Glu Thr Cys Leu Ser  Thr Ser Glu Pro Ser  Ala Arg Val
    1140                 1145                 1150

cca gat  tcc gtg ggt gtg tcc  cca gat gac ctg gat  gac act ggg     4064
Pro Asp  Ser Val Gly Val Ser  Pro Asp Asp Leu Asp  Asp Thr Gly
    1155                 1160                 1165

cag cca  gtc ctt gag cga ggc  cag ctc aat ggg aag  cgg gac acc     4109
Gln Pro  Val Leu Glu Arg Gly  Gln Leu Asn Gly Lys  Arg Asp Thr
    1170                 1175                 1180

ctg tgg  ctg gcg ctg agg gag  aca gtg tat gac cca  tca ttg ccc     4154
Leu Trp  Leu Ala Leu Arg Glu  Thr Val Tyr Asp Pro  Ser Leu Pro
    1185                 1190                 1195

gct tcc  cat cac agc agc ttg  tcc tgg aag ggc cga  ggg ggg cca     4199
Ala Ser  His His Ser Ser Leu  Ser Trp Lys Gly Arg  Gly Gly Pro
    1200                 1205                 1210

ggg gat  ggc agc cct gtg gtg  ctg ccc aat agc cag  cca gac ctg     4244
Gly Asp  Gly Ser Pro Val Val  Leu Pro Asn Ser Gln  Pro Asp Leu
    1215                 1220                 1225

cca gat  gtt tgg ctg cgc agg  ccc agc act cac acg  tca ggc tat     4289
```

```
Pro Asp  Val Trp Leu Arg Arg  Pro Ser Thr His Thr  Ser Gly Tyr
    1230                 1235                 1240

agc agc  tgagggggac ccggggaggc tggacagggc gcggaaccct gtcatggatg     4345
Ser Ser
    1245

acaaggcaag ggcagcaata ggctggagcc cgaaggtatt tctccagatc cacagggaga   4405

ggtctcaccc tccagctgtg gatgttaaac cctgccagat gtcccagcct tgatctgtct   4465

gctcctactc ctcacatctg gaggattcca gcaggagggg ttttggaggg gacctgcttg   4525

cgacctgctg agggcttgtc tgctcccaca gcaccatcta agacccctcc tctagaagtg   4585

gggaaggcca gatgtgtagc ttcgggtatc agaggaggct gacctggccc ccatcccaag   4645

ttacaagaac ttcagtgaga ctaagggacc cccatcctag ggatcttgtc agggttcctt   4705

actgaccaga ggagcccgca gcaatctcca cagcctcctg ggtctcaccc ctttcatggg   4765

ctcttcatca ggacacttcc ctctcttttg ggagcttctc tgggcagaat tgggctggga   4825

cctctctccc caactgccct gctctcctca tactcaccgg tttgaccaga aattctccaa   4885

atccagccat agatggctgc tgggtgtgca gcaggagaag gaggatggtc agccttggag   4945

catctctcaa ttacgggaca gtccctcttt ggaagcaggc tcctgtgctt tcctgtgtta   5005

ataaacagta ataatccttt ccatctctgc                                    5035


<210> SEQ ID NO 2
<211> LENGTH: 4479
<212> TYPE: DNA
<213> ORGANISM: Homo sapiens
<220> FEATURE:
<221> NAME/KEY: CDS
<222> LOCATION: (1)..(4476)

<400> SEQUENCE: 2

atg gga aga aag acc caa cct gat gcc tcg ccc cac tgg gga ggg gag      48
Met Gly Arg Lys Thr Gln Pro Asp Ala Ser Pro His Trp Gly Gly Glu
1               5                   10                  15

gag ggc gct gag cga gcc ggg aac ctc gca ggc ctg aag ccg ccc gcc      96
Glu Gly Ala Glu Arg Ala Gly Asn Leu Ala Gly Leu Lys Pro Pro Ala
            20                  25                  30

tcg acc cgg ggc gtc cag cgt ggt gaa gtg cgg gcg tgg agc tcg ccc     144
Ser Thr Arg Gly Val Gln Arg Gly Glu Val Arg Ala Trp Ser Ser Pro
        35                  40                  45

tct atc cgg ctg gaa gga gcc tac gca tgc gca cga gca ccc cgc cgc     192
Ser Ile Arg Leu Glu Gly Ala Tyr Ala Cys Ala Arg Ala Pro Arg Arg
    50                  55                  60

cgc tgc cgc cgc cac cgc cgc cgc cgc cgc cgc cgc cgc ggc ttc agc     240
Arg Cys Arg Arg His Arg Arg Arg Arg Arg Arg Arg Arg Gly Phe Ser
65                  70                  75                  80

acc agc gcc cgg aca gcg gtg ccg ccc acg ggc atg gac ggt gac agc     288
Thr Ser Ala Arg Thr Ala Val Pro Pro Thr Gly Met Asp Gly Asp Ser
                85                  90                  95

agc agc agc agc ggc ggc agc ggt ccg gct ccc ggc ccg ggt ccg gaa     336
Ser Ser Ser Ser Gly Gly Ser Gly Pro Ala Pro Gly Pro Gly Pro Glu
            100                 105                 110

ggg gag caa cgg ccc gag ggg gag ccc ttg gcc cca gac ggc ggc tcc     384
Gly Glu Gln Arg Pro Glu Gly Glu Pro Leu Ala Pro Asp Gly Gly Ser
        115                 120                 125

ccg gac agc acc cag acc aag gct gtg ccc cct gag gca agc cca gag     432
Pro Asp Ser Thr Gln Thr Lys Ala Val Pro Pro Glu Ala Ser Pro Glu
    130                 135                 140

aga agc tgc tcc ctc cac agc tgc ccc ctg gag gac cct tcc agc tct     480
Arg Ser Cys Ser Leu His Ser Cys Pro Leu Glu Asp Pro Ser Ser Ser
```

```
145                 150                 155                 160

tca gga ccc cca cca aca act tcc acc ctc cag cct gtg ggt cca tcc       528
Ser Gly Pro Pro Pro Thr Thr Ser Thr Leu Gln Pro Val Gly Pro Ser
                165                 170                 175

agc ccc ttg gcc cct gcc cac ttc acc tat ccc cgg gca ctg cag gaa       576
Ser Pro Leu Ala Pro Ala His Phe Thr Tyr Pro Arg Ala Leu Gln Glu
            180                 185                 190

tac cag ggg ggc agt tcc ctg cca gga ctt ggg gat cgg gca gct ctc       624
Tyr Gln Gly Gly Ser Ser Leu Pro Gly Leu Gly Asp Arg Ala Ala Leu
        195                 200                 205

tgc tcc cac ggc tcc agc ctc agc cct tct cca gcc ccc tca cag cgc       672
Cys Ser His Gly Ser Ser Leu Ser Pro Ser Pro Ala Pro Ser Gln Arg
    210                 215                 220

gat ggg acc tgg aag cca ccc gct gtg cag cac cat gtg gtc agc gtc       720
Asp Gly Thr Trp Lys Pro Pro Ala Val Gln His His Val Val Ser Val
225                 230                 235                 240

agg cag gaa cga gcc ttc cag atg cca aag agc tat tcc cag ctg att       768
Arg Gln Glu Arg Ala Phe Gln Met Pro Lys Ser Tyr Ser Gln Leu Ile
                245                 250                 255

gct gag tgg cca gtg gcc gtg ctg atg ctg tgt ctg gct gtc atc ttc       816
Ala Glu Trp Pro Val Ala Val Leu Met Leu Cys Leu Ala Val Ile Phe
            260                 265                 270

ctc tgc acc ctg gct gga ctg ttg ggg gcc cgg ctg ccc gac ttc tcc       864
Leu Cys Thr Leu Ala Gly Leu Leu Gly Ala Arg Leu Pro Asp Phe Ser
        275                 280                 285

aag cct ttg ctg ggc ttt gag cca cgg gac aca gac att ggg agc aag       912
Lys Pro Leu Leu Gly Phe Glu Pro Arg Asp Thr Asp Ile Gly Ser Lys
    290                 295                 300

tta gtg gtc tgg aga gca cta caa gcc ctc aca ggc ccc agg aag ctg       960
Leu Val Val Trp Arg Ala Leu Gln Ala Leu Thr Gly Pro Arg Lys Leu
305                 310                 315                 320

ctt ttc ctt tcc cca gac ctt gag ctg aac agc tcg agc tcc cac aac      1008
Leu Phe Leu Ser Pro Asp Leu Glu Leu Asn Ser Ser Ser Ser His Asn
                325                 330                 335

act ctg agg cct gca ccc aga ggc agt gcc cag gag agc gct gtc cgg      1056
Thr Leu Arg Pro Ala Pro Arg Gly Ser Ala Gln Glu Ser Ala Val Arg
            340                 345                 350

cct cgg aga atg gtg gag ccc ctg gag gac aga agg caa gag aac ttc      1104
Pro Arg Arg Met Val Glu Pro Leu Glu Asp Arg Arg Gln Glu Asn Phe
        355                 360                 365

ttc tgt ggc ccc cct gag aag agc tat gca aag ctg gtg ttc atg tcc      1152
Phe Cys Gly Pro Pro Glu Lys Ser Tyr Ala Lys Leu Val Phe Met Ser
    370                 375                 380

acc tcc tcg ggc agc cta tgg aac ctg cat gcc atc cat tcc atg tgt      1200
Thr Ser Ser Gly Ser Leu Trp Asn Leu His Ala Ile His Ser Met Cys
385                 390                 395                 400

cgc atg gaa cag gac cag atc cgc tcc cat acc agc ttc ggg gct ctg      1248
Arg Met Glu Gln Asp Gln Ile Arg Ser His Thr Ser Phe Gly Ala Leu
                405                 410                 415

tgc cag cgg aca gca gcc aac cag tgc tgc ccc agc tgg tcc ctg ggc      1296
Cys Gln Arg Thr Ala Ala Asn Gln Cys Cys Pro Ser Trp Ser Leu Gly
            420                 425                 430

aac tat ctg gct gtg ctc tcc aac cgc tcc tcc tgc ctg gac act acc      1344
Asn Tyr Leu Ala Val Leu Ser Asn Arg Ser Ser Cys Leu Asp Thr Thr
        435                 440                 445

caa gct gac gca gcc cgc aca ctg gcc ctg ctt cgg acc tgt gcc ctc      1392
Gln Ala Asp Ala Ala Arg Thr Leu Ala Leu Leu Arg Thr Cys Ala Leu
    450                 455                 460

tac tac cac agt ggc gcc ttg gtg ccc tct tgt ctg gga cct ggg cag      1440
Tyr Tyr His Ser Gly Ala Leu Val Pro Ser Cys Leu Gly Pro Gly Gln
```

```
465                 470                 475                 480

aac aag tcc cca cgc tgt gcc cag gtt ccc acc aag tgc tcc cag agt      1488
Asn Lys Ser Pro Arg Cys Ala Gln Val Pro Thr Lys Cys Ser Gln Ser
                485                 490                 495

agt gcc atc tac caa ctc ctg cac ttt ctg ctt gac agg gac ttt ctg      1536
Ser Ala Ile Tyr Gln Leu Leu His Phe Leu Leu Asp Arg Asp Phe Leu
            500                 505                 510

agt ccc cag acc act gac tac cag gtg cct tcc ctc aag tac agc ctg      1584
Ser Pro Gln Thr Thr Asp Tyr Gln Val Pro Ser Leu Lys Tyr Ser Leu
        515                 520                 525

ctc ttc ctg ccc acc cca aag ggt gct tcc ctc atg gac atc tac ctg      1632
Leu Phe Leu Pro Thr Pro Lys Gly Ala Ser Leu Met Asp Ile Tyr Leu
    530                 535                 540

gac cgg ctg gcc acc ccc tgg ggg ctt gct gac aac tac acc tct gtc      1680
Asp Arg Leu Ala Thr Pro Trp Gly Leu Ala Asp Asn Tyr Thr Ser Val
545                 550                 555                 560

act ggc atg gac ctg ggc ctc aag cag gag ctg ctg agg cac ttc ctg      1728
Thr Gly Met Asp Leu Gly Leu Lys Gln Glu Leu Leu Arg His Phe Leu
                565                 570                 575

gtc cag gac acg gtg tac ccc ttg ctg gct ctg gtt gcc atc ttc ttc      1776
Val Gln Asp Thr Val Tyr Pro Leu Leu Ala Leu Val Ala Ile Phe Phe
            580                 585                 590

ggc atg gcc ctg tac ctg cgc tca ctc ttc ctc acg ctc atg gtg ctg      1824
Gly Met Ala Leu Tyr Leu Arg Ser Leu Phe Leu Thr Leu Met Val Leu
        595                 600                 605

ctg ggg gtg ctg ggc tca ctg ctg gtg gcc ttc ttc ctt tac cag gtg      1872
Leu Gly Val Leu Gly Ser Leu Leu Val Ala Phe Phe Leu Tyr Gln Val
    610                 615                 620

gcc ttc cgc atg gcc tac ttc ccc ttc gtc aat ctg gca gcc ctc ctc      1920
Ala Phe Arg Met Ala Tyr Phe Pro Phe Val Asn Leu Ala Ala Leu Leu
625                 630                 635                 640

ctg ctg agc agc gtc tgc gcc aac cac acg ctc atc ttc ttc gac ctg      1968
Leu Leu Ser Ser Val Cys Ala Asn His Thr Leu Ile Phe Phe Asp Leu
                645                 650                 655

tgg cgc ctt agc aag agc cag ctg ccg tcg ggg ggg ctg gcg cag cgc      2016
Trp Arg Leu Ser Lys Ser Gln Leu Pro Ser Gly Gly Leu Ala Gln Arg
            660                 665                 670

gtg ggc cgc acc atg cac cac ttc ggc tac ctg ctg ctg gtc tcc ggc      2064
Val Gly Arg Thr Met His His Phe Gly Tyr Leu Leu Leu Val Ser Gly
        675                 680                 685

ctc acc acg agc gcg gcc ttc tat gcc agc tac ctg agc cgc ctg ccg      2112
Leu Thr Thr Ser Ala Ala Phe Tyr Ala Ser Tyr Leu Ser Arg Leu Pro
    690                 695                 700

gcc gtt cgc tgc ctc gcc ctc ttc atg ggc acg gct gtg ctg gtg cac      2160
Ala Val Arg Cys Leu Ala Leu Phe Met Gly Thr Ala Val Leu Val His
705                 710                 715                 720

ctg gcg ctc acg ctg gtc tgg ctg ccc gcc tcc gcc gtg ctc cac gag      2208
Leu Ala Leu Thr Leu Val Trp Leu Pro Ala Ser Ala Val Leu His Glu
                725                 730                 735

cgc tac ctg gcg cgc ggc tgt gcg cgc cgg gcg cgg ggc cgg tgg gag      2256
Arg Tyr Leu Ala Arg Gly Cys Ala Arg Arg Ala Arg Gly Arg Trp Glu
            740                 745                 750

ggc agc gcg ccc cgg cgg cta ctg ctg gcg ctg cac cgg cgg ctc cgc      2304
Gly Ser Ala Pro Arg Arg Leu Leu Leu Ala Leu His Arg Arg Leu Arg
        755                 760                 765

ggc ctg cgg agg gcg gcg gct ggc acc tcg cgt ctg ctc ttc cag cgc      2352
Gly Leu Arg Arg Ala Ala Ala Gly Thr Ser Arg Leu Leu Phe Gln Arg
    770                 775                 780

ctg ctg ccc tgc ggc gtc atc aag ttc cgc tac atc tgg atc tgc tgg      2400
Leu Leu Pro Cys Gly Val Ile Lys Phe Arg Tyr Ile Trp Ile Cys Trp
```

```
785                 790                 795                 800

ttc gca gca ctg gcg gca ggg ggc gcc tac atc gcc gga gtc agc ccc      2448
Phe Ala Ala Leu Ala Ala Gly Gly Ala Tyr Ile Ala Gly Val Ser Pro
                805                 810                 815

cgc ctg cgg ctg ccc acg ctg ccg ccg ccc ggc ggc cag gtc ttc cgg      2496
Arg Leu Arg Leu Pro Thr Leu Pro Pro Pro Gly Gly Gln Val Phe Arg
            820                 825                 830

ccc agc cac ccc ttc gag cgc ttc gac gcg gag tat cgc cag ctg ttc      2544
Pro Ser His Pro Phe Glu Arg Phe Asp Ala Glu Tyr Arg Gln Leu Phe
        835                 840                 845

ctg ttc gag cag ctg ccg cag ggc gag ggc ggc cac atg ccc gtg gtt      2592
Leu Phe Glu Gln Leu Pro Gln Gly Glu Gly Gly His Met Pro Val Val
    850                 855                 860

ttg gtg tgg ggc gtc ctg cct gtg gac act ggc gac cct ctg gac cct      2640
Leu Val Trp Gly Val Leu Pro Val Asp Thr Gly Asp Pro Leu Asp Pro
865                 870                 875                 880

cgt agc aac agc agc ctg gtg agg gac cct gcc ttc tcg gcc agc ggc      2688
Arg Ser Asn Ser Ser Leu Val Arg Asp Pro Ala Phe Ser Ala Ser Gly
                885                 890                 895

cct gag gcc cag cgc tgg ctg ctg gca ctc tgt cac cgg gcc cgg aat      2736
Pro Glu Ala Gln Arg Trp Leu Leu Ala Leu Cys His Arg Ala Arg Asn
            900                 905                 910

cag agc ttc ttc gac acc ctg cag gaa ggc tgg ccc acg ctg tgt ttc      2784
Gln Ser Phe Phe Asp Thr Leu Gln Glu Gly Trp Pro Thr Leu Cys Phe
        915                 920                 925

gtg gag acc ctc cag cgc tgg atg gag agc ccc agc tgc gcc cgc ctg      2832
Val Glu Thr Leu Gln Arg Trp Met Glu Ser Pro Ser Cys Ala Arg Leu
    930                 935                 940

ggg cct gac ctc tgc tgc ggc cac tcg gac ttc ccc tgg gcc ccc cag      2880
Gly Pro Asp Leu Cys Cys Gly His Ser Asp Phe Pro Trp Ala Pro Gln
945                 950                 955                 960

ttt ttc ctg cac tgc ctg aaa atg atg gct ctg gag caa ggc ccc gat      2928
Phe Phe Leu His Cys Leu Lys Met Met Ala Leu Glu Gln Gly Pro Asp
                965                 970                 975

ggc acc cag gac ctg gga ctc cgc ttt gat gcc cat ggc agc ctg gcc      2976
Gly Thr Gln Asp Leu Gly Leu Arg Phe Asp Ala His Gly Ser Leu Ala
            980                 985                 990

gcc ctg gtc cta caa ttc cag acc  aac ttc cgg aac agt  ccg gac tac    3024
Ala Leu Val Leu Gln Phe Gln Thr  Asn Phe Arg Asn Ser  Pro Asp Tyr
        995                 1000                1005

aac cag  acc cag ctc ttc tac  aat gag gtc agc cac  tgg ctg gca      3069
Asn Gln  Thr Gln Leu Phe Tyr  Asn Glu Val Ser His  Trp Leu Ala
    1010                1015                1020

gcg gag  ctg ggc atg gca cct  cca ggc ctc cgc cgt  ggt tgg ttc      3114
Ala Glu  Leu Gly Met Ala Pro  Pro Gly Leu Arg Arg  Gly Trp Phe
    1025                1030                1035

act agc  cgt cta gag ctg tat  agc ctg cag cac agc  ctg agc act      3159
Thr Ser  Arg Leu Glu Leu Tyr  Ser Leu Gln His Ser  Leu Ser Thr
    1040                1045                1050

gag cct  gct gtg gtg ctg ggc  ctg gct ttg gcg ctg  gcc ttt gcc      3204
Glu Pro  Ala Val Val Leu Gly  Leu Ala Leu Ala Leu  Ala Phe Ala
    1055                1060                1065

aca ctg  ctc ctg ggc acc tgg  aat gtt ccc ctc agc  cta ttc tcc      3249
Thr Leu  Leu Leu Gly Thr Trp  Asn Val Pro Leu Ser  Leu Phe Ser
    1070                1075                1080

gtg gca  gct gtg gca ggc acc  gtg ctg ctc act gta  gga ctc ctg      3294
Val Ala  Ala Val Ala Gly Thr  Val Leu Leu Thr Val  Gly Leu Leu
    1085                1090                1095

gtt ctc  ctc gag tgg cag ctc  aac act gcc gag gcc  ctg ttt ctc      3339
Val Leu  Leu Glu Trp Gln Leu  Asn Thr Ala Glu Ala  Leu Phe Leu
```

-continued

```
    1100                1105                1110

tct gcc  tca gtg ggc ctc tca  gta gac ttc act gtc  aac tac tgc      3384
Ser Ala  Ser Val Gly Leu Ser  Val Asp Phe Thr Val  Asn Tyr Cys
    1115                1120                1125

atc tcc  tat cac ctg tgc cca  cac cct gac cgc ctg  agc cgt gtg      3429
Ile Ser  Tyr His Leu Cys Pro  His Pro Asp Arg Leu  Ser Arg Val
    1130                1135                1140

gcc ttc  tct ctg cgc cag acc  agc tgc gcc aca gcc  gtg ggg gct      3474
Ala Phe  Ser Leu Arg Gln Thr  Ser Cys Ala Thr Ala  Val Gly Ala
    1145                1150                1155

gca gcc  ctg ttt gcg gca ggc  gtg ctc atg ctg cct  gcc aca gtg      3519
Ala Ala  Leu Phe Ala Ala Gly  Val Leu Met Leu Pro  Ala Thr Val
    1160                1165                1170

ctg ctc  tat cgc aag ctg ggc  atc atc ctc atg atg  gtc aaa tgc      3564
Leu Leu  Tyr Arg Lys Leu Gly  Ile Ile Leu Met Met  Val Lys Cys
    1175                1180                1185

gtc agt  tgt ggc ttt gcc agc  ttc ttc ttc caa tct  ctc tgc tgt      3609
Val Ser  Cys Gly Phe Ala Ser  Phe Phe Phe Gln Ser  Leu Cys Cys
    1190                1195                1200

ttc ttc  ggg cca gag aag aac  tgt ggg cag atc ctc  tgg ccc tgt      3654
Phe Phe  Gly Pro Glu Lys Asn  Cys Gly Gln Ile Leu  Trp Pro Cys
    1205                1210                1215

gcc cac  ctg cca tgg gat gct  ggt act ggg gac cct  ggt ggg gag      3699
Ala His  Leu Pro Trp Asp Ala  Gly Thr Gly Asp Pro  Gly Gly Glu
    1220                1225                1230

aag gca  ggc cgc cca cga cca  ggg tca gtg gga ggg  atg ccc ggg      3744
Lys Ala  Gly Arg Pro Arg Pro  Gly Ser Val Gly Gly  Met Pro Gly
    1235                1240                1245

tcc tgc  tca gag caa tat gag  cta cag ccc ctg gca  cgg cgt cgg      3789
Ser Cys  Ser Glu Gln Tyr Glu  Leu Gln Pro Leu Ala  Arg Arg Arg
    1250                1255                1260

agc ccc  agc ttt gac acc agc  aca gcc acc agc aag  ctg tcc cac      3834
Ser Pro  Ser Phe Asp Thr Ser  Thr Ala Thr Ser Lys  Leu Ser His
    1265                1270                1275

cgg ccc  tca gta ctc tct gag  gat ctg cag ctc cat  gat ggt ccg      3879
Arg Pro  Ser Val Leu Ser Glu  Asp Leu Gln Leu His  Asp Gly Pro
    1280                1285                1290

tgc tgt  tcc cgg ccc cca cca  gcc cct gcc tcc cca  agg gag ctg      3924
Cys Cys  Ser Arg Pro Pro Pro  Ala Pro Ala Ser Pro  Arg Glu Leu
    1295                1300                1305

ctg ctg  gac cac cag gca gtc  ttc agc cag tgc cct  gcc ctg cag      3969
Leu Leu  Asp His Gln Ala Val  Phe Ser Gln Cys Pro  Ala Leu Gln
    1310                1315                1320

acc tcc  tcc ccc tat aag cag  gct ggc ccc agc ccc  aaa acc cgg      4014
Thr Ser  Ser Pro Tyr Lys Gln  Ala Gly Pro Ser Pro  Lys Thr Arg
    1325                1330                1335

gcc agg  cag gac tcc caa ggg  gag gag gct gag ccc  ctg cca gcc      4059
Ala Arg  Gln Asp Ser Gln Gly  Glu Glu Ala Glu Pro  Leu Pro Ala
    1340                1345                1350

tca cca  gaa gcc cca gcc cac  tct cct aag gcc aag  gct gca gat      4104
Ser Pro  Glu Ala Pro Ala His  Ser Pro Lys Ala Lys  Ala Ala Asp
    1355                1360                1365

cct cct  gat ggc ttc tgt tcc  tca gcc agc acc ctg  gag ggg ctc      4149
Pro Pro  Asp Gly Phe Cys Ser  Ser Ala Ser Thr Leu  Glu Gly Leu
    1370                1375                1380

agc gtc  tct gat gag acc tgc  cta agc acc tct gag  ccc agt gcc      4194
Ser Val  Ser Asp Glu Thr Cys  Leu Ser Thr Ser Glu  Pro Ser Ala
    1385                1390                1395

cgt gta  cca gat tcc gtg ggt  gtg tcc cca gat gac  ctg gat gac      4239
Arg Val  Pro Asp Ser Val Gly  Val Ser Pro Asp Asp  Leu Asp Asp
```

-continued

```
    1400                1405                1410

act ggg  cag cca gtc ctt gag  cga ggc cag ctc aat  ggg aag cgg      4284
Thr Gly  Gln Pro Val Leu Glu  Arg Gly Gln Leu Asn  Gly Lys Arg
    1415                1420                1425

gac acc  ctg tgg ctg gcg ctg  agg gag aca gtg tat  gac cca tca      4329
Asp Thr  Leu Trp Leu Ala Leu  Arg Glu Thr Val Tyr  Asp Pro Ser
    1430                1435                1440

ttg ccc  gct tcc cat cac agc  agc ttg tcc tgg aag  ggc cga ggg      4374
Leu Pro  Ala Ser His His Ser  Ser Leu Ser Trp Lys  Gly Arg Gly
    1445                1450                1455

ggg cca  ggg gat ggc agc cct  gtg gtg ctg ccc aat  agc cag cca      4419
Gly Pro  Gly Asp Gly Ser Pro  Val Val Leu Pro Asn  Ser Gln Pro
    1460                1465                1470

gac ctg  cca gat gtt tgg ctg  cgc agg ccc agc act  cac acg tca      4464
Asp Leu  Pro Asp Val Trp Leu  Arg Arg Pro Ser Thr  His Thr Ser
    1475                1480                1485

ggc tat  agc agc tga                                                4479
Gly Tyr  Ser Ser
    1490
```

<210> SEQ ID NO 3
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 3
gactagttct agatcgcgag cggccgccct ttttttttt tttt 44

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer 1742-3538

<400> SEQUENCE: 4
cagcactcac acgtcaggct 20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer 1742-3658

<400> SEQUENCE: 5
agaaatacct tcgggctcca g 21

<210> SEQ ID NO 6
<211> LENGTH: 25
<212> TYPE: PRT
<213> ORGANISM: Homo sapiens

<400> SEQUENCE: 6

```
Val Ala Val Leu Met Leu Cys Leu Ala Val Ile Phe Leu Cys Thr Leu
1               5                   10                  15

Ala Gly Leu Leu Gly Ala Arg Leu Pro
            20                  25
```

<210> SEQ ID NO 7
<211> LENGTH: 25
<212> TYPE: PRT

```
<213> ORGANISM: Homo sapiens

<400> SEQUENCE: 7

Leu Val Gln Asp Thr Val Tyr Pro Leu Leu Ala Leu Val Ala Ile Phe
1               5                   10                  15

Phe Gly Met Ala Leu Tyr Leu Arg Ser
            20                  25


<210> SEQ ID NO 8
<211> LENGTH: 25
<212> TYPE: PRT
<213> ORGANISM: Homo sapiens

<400> SEQUENCE: 8

Thr Leu Met Val Leu Leu Gly Val Leu Gly Ser Leu Leu Val Ala Phe
1               5                   10                  15

Phe Leu Tyr Gln Val Ala Phe Arg Met
            20                  25


<210> SEQ ID NO 9
<211> LENGTH: 25
<212> TYPE: PRT
<213> ORGANISM: Homo sapiens

<400> SEQUENCE: 9

Pro Phe Val Asn Leu Ala Ala Leu Leu Leu Leu Ser Ser Val Cys Ala
1               5                   10                  15

Asn His Thr Leu Ile Phe Phe Asp Leu
            20                  25


<210> SEQ ID NO 10
<211> LENGTH: 25
<212> TYPE: PRT
<213> ORGANISM: Homo sapiens

<400> SEQUENCE: 10

Phe Gly Tyr Leu Leu Leu Val Ser Gly Leu Thr Thr Ser Ala Ala Phe
1               5                   10                  15

Tyr Ala Ser Tyr Leu Ser Arg Leu Pro
            20                  25


<210> SEQ ID NO 11
<211> LENGTH: 25
<212> TYPE: PRT
<213> ORGANISM: Homo sapiens

<400> SEQUENCE: 11

Ala Leu Phe Met Gly Thr Ala Val Leu Val His Leu Ala Leu Thr Leu
1               5                   10                  15

Val Trp Leu Pro Ala Ser Ala Val Leu
            20                  25


<210> SEQ ID NO 12
<211> LENGTH: 25
<212> TYPE: PRT
<213> ORGANISM: Homo sapiens

<400> SEQUENCE: 12

Phe Gln Arg Leu Leu Pro Cys Gly Val Ile Lys Phe Arg Tyr Ile Trp
1               5                   10                  15

Ile Cys Trp Phe Ala Ala Leu Ala Ala
            20                  25
```

<210> SEQ ID NO 13
<211> LENGTH: 25
<212> TYPE: PRT
<213> ORGANISM: Homo sapiens

<400> SEQUENCE: 13

```
Ser Leu Ser Thr Glu Pro Ala Val Val Leu Gly Leu Ala Leu Ala Leu
1               5                   10                  15

Ala Phe Ala Thr Leu Leu Leu Gly Thr
            20                  25
```

<210> SEQ ID NO 14
<211> LENGTH: 25
<212> TYPE: PRT
<213> ORGANISM: Homo sapiens

<400> SEQUENCE: 14

```
Pro Leu Ser Leu Phe Ser Val Ala Ala Val Ala Gly Thr Val Leu Leu
1               5                   10                  15

Thr Val Gly Leu Leu Val Leu Leu Glu
            20                  25
```

<210> SEQ ID NO 15
<211> LENGTH: 25
<212> TYPE: PRT
<213> ORGANISM: Homo sapiens

<400> SEQUENCE: 15

```
Leu Phe Leu Ser Ala Ser Val Gly Leu Ser Val Asp Phe Thr Val Asn
1               5                   10                  15

Tyr Cys Ile Ser Tyr His Leu Cys Pro
            20                  25
```

<210> SEQ ID NO 16
<211> LENGTH: 25
<212> TYPE: PRT
<213> ORGANISM: Homo sapiens

<400> SEQUENCE: 16

```
Gln Thr Ser Cys Ala Thr Ala Val Gly Ala Ala Ala Leu Phe Ala Ala
1               5                   10                  15

Gly Val Leu Met Leu Pro Ala Thr Val
            20                  25
```

<210> SEQ ID NO 17
<211> LENGTH: 25
<212> TYPE: PRT
<213> ORGANISM: Homo sapiens

<400> SEQUENCE: 17

```
Ile Ile Leu Met Met Val Lys Cys Val Ser Cys Gly Phe Ala Ser Phe
1               5                   10                  15

Phe Phe Gln Ser Leu Cys Cys Phe Phe
            20                  25
```

<210> SEQ ID NO 18
<211> LENGTH: 1245
<212> TYPE: PRT
<213> ORGANISM: Homo sapiens
<220> FEATURE:
<221> NAME/KEY: MISC_FEATURE
<223> OTHER INFORMATION: Amino acid sequence of SEQ ID NO: 1

<400> SEQUENCE: 18

```
Met Pro Lys Ser Tyr Ser Gln Leu Ile Ala Glu Trp Pro Val Ala Val
1               5                   10                  15

Leu Met Leu Cys Leu Ala Val Ile Phe Leu Cys Thr Leu Ala Gly Leu
            20                  25                  30

Leu Gly Ala Arg Leu Pro Asp Phe Ser Lys Pro Leu Leu Gly Phe Glu
        35                  40                  45

Pro Arg Asp Thr Asp Ile Gly Ser Lys Leu Val Val Trp Arg Ala Leu
    50                  55                  60

Gln Ala Leu Thr Gly Pro Arg Lys Leu Leu Phe Leu Ser Pro Asp Leu
65                  70                  75                  80

Glu Leu Asn Ser Ser Ser Ser His Asn Thr Leu Arg Pro Ala Pro Arg
                85                  90                  95

Gly Ser Ala Gln Glu Ser Ala Val Arg Pro Arg Arg Met Val Glu Pro
            100                 105                 110

Leu Glu Asp Arg Arg Gln Glu Asn Phe Phe Cys Gly Pro Pro Glu Lys
        115                 120                 125

Ser Tyr Ala Lys Leu Val Phe Met Ser Thr Ser Ser Gly Ser Leu Trp
    130                 135                 140

Asn Leu His Ala Ile His Ser Met Cys Arg Met Glu Gln Asp Gln Ile
145                 150                 155                 160

Arg Ser His Thr Ser Phe Gly Ala Leu Cys Gln Arg Thr Ala Ala Asn
                165                 170                 175

Gln Cys Cys Pro Ser Trp Ser Leu Gly Asn Tyr Leu Ala Val Leu Ser
            180                 185                 190

Asn Arg Ser Ser Cys Leu Asp Thr Thr Gln Ala Asp Ala Ala Arg Thr
        195                 200                 205

Leu Ala Leu Leu Arg Thr Cys Ala Leu Tyr Tyr His Ser Gly Ala Leu
    210                 215                 220

Val Pro Ser Cys Leu Gly Pro Gly Gln Asn Lys Ser Pro Arg Cys Ala
225                 230                 235                 240

Gln Val Pro Thr Lys Cys Ser Gln Ser Ser Ala Ile Tyr Gln Leu Leu
                245                 250                 255

His Phe Leu Leu Asp Arg Asp Phe Leu Ser Pro Gln Thr Thr Asp Tyr
            260                 265                 270

Gln Val Pro Ser Leu Lys Tyr Ser Leu Leu Phe Leu Pro Thr Pro Lys
        275                 280                 285

Gly Ala Ser Leu Met Asp Ile Tyr Leu Asp Arg Leu Ala Thr Pro Trp
    290                 295                 300

Gly Leu Ala Asp Asn Tyr Thr Ser Val Thr Gly Met Asp Leu Gly Leu
305                 310                 315                 320

Lys Gln Glu Leu Leu Arg His Phe Leu Val Gln Asp Thr Val Tyr Pro
                325                 330                 335

Leu Leu Ala Leu Val Ala Ile Phe Phe Gly Met Ala Leu Tyr Leu Arg
            340                 345                 350

Ser Leu Phe Leu Thr Leu Met Val Leu Leu Gly Val Leu Gly Ser Leu
        355                 360                 365

Leu Val Ala Phe Phe Leu Tyr Gln Val Ala Phe Arg Met Ala Tyr Phe
    370                 375                 380

Pro Phe Val Asn Leu Ala Ala Leu Leu Leu Leu Ser Ser Val Cys Ala
385                 390                 395                 400

Asn His Thr Leu Ile Phe Phe Asp Leu Trp Arg Leu Ser Lys Ser Gln
                405                 410                 415

Leu Pro Ser Gly Gly Leu Ala Gln Arg Val Gly Arg Thr Met His His
```

```
            420                 425                 430

Phe Gly Tyr Leu Leu Leu Val Ser Gly Leu Thr Thr Ser Ala Ala Phe
        435                 440                 445

Tyr Ala Ser Tyr Leu Ser Arg Leu Pro Ala Val Arg Cys Leu Ala Leu
    450                 455                 460

Phe Met Gly Thr Ala Val Leu Val His Leu Ala Leu Thr Leu Val Trp
465                 470                 475                 480

Leu Pro Ala Ser Ala Val Leu His Glu Arg Tyr Leu Ala Arg Gly Cys
                485                 490                 495

Ala Arg Arg Ala Arg Gly Arg Trp Glu Gly Ser Ala Pro Arg Arg Leu
            500                 505                 510

Leu Leu Ala Leu His Arg Arg Leu Arg Gly Leu Arg Arg Ala Ala Ala
        515                 520                 525

Gly Thr Ser Arg Leu Leu Phe Gln Arg Leu Leu Pro Cys Gly Val Ile
    530                 535                 540

Lys Phe Arg Tyr Ile Trp Ile Cys Trp Phe Ala Ala Leu Ala Ala Gly
545                 550                 555                 560

Gly Ala Tyr Ile Ala Gly Val Ser Pro Arg Leu Arg Leu Pro Thr Leu
                565                 570                 575

Pro Pro Pro Gly Gly Gln Val Phe Arg Pro Ser His Pro Phe Glu Arg
            580                 585                 590

Phe Asp Ala Glu Tyr Arg Gln Leu Phe Leu Phe Glu Gln Leu Pro Gln
        595                 600                 605

Gly Glu Gly Gly His Met Pro Val Val Leu Val Trp Gly Val Leu Pro
    610                 615                 620

Val Asp Thr Gly Asp Pro Leu Asp Pro Arg Ser Asn Ser Ser Leu Val
625                 630                 635                 640

Arg Asp Pro Ala Phe Ser Ala Ser Gly Pro Glu Ala Gln Arg Trp Leu
                645                 650                 655

Leu Ala Leu Cys His Arg Ala Arg Asn Gln Ser Phe Phe Asp Thr Leu
            660                 665                 670

Gln Glu Gly Trp Pro Thr Leu Cys Phe Val Glu Thr Leu Gln Arg Trp
        675                 680                 685

Met Glu Ser Pro Ser Cys Ala Arg Leu Gly Pro Asp Leu Cys Cys Gly
    690                 695                 700

His Ser Asp Phe Pro Trp Ala Pro Gln Phe Phe Leu His Cys Leu Lys
705                 710                 715                 720

Met Met Ala Leu Glu Gln Gly Pro Asp Gly Thr Gln Asp Leu Gly Leu
                725                 730                 735

Arg Phe Asp Ala His Gly Ser Leu Ala Ala Leu Val Leu Gln Phe Gln
            740                 745                 750

Thr Asn Phe Arg Asn Ser Pro Asp Tyr Asn Gln Thr Gln Leu Phe Tyr
        755                 760                 765

Asn Glu Val Ser His Trp Leu Ala Ala Glu Leu Gly Met Ala Pro Pro
    770                 775                 780

Gly Leu Arg Arg Gly Trp Phe Thr Ser Arg Leu Glu Leu Tyr Ser Leu
785                 790                 795                 800

Gln His Ser Leu Ser Thr Glu Pro Ala Val Val Leu Gly Leu Ala Leu
                805                 810                 815

Ala Leu Ala Phe Ala Thr Leu Leu Leu Gly Thr Trp Asn Val Pro Leu
            820                 825                 830

Ser Leu Phe Ser Val Ala Ala Val Ala Gly Thr Val Leu Leu Thr Val
        835                 840                 845
```

```
Gly Leu Leu Val Leu Leu Glu Trp Gln Leu Asn Thr Ala Glu Ala Leu
    850                 855                 860

Phe Leu Ser Ala Ser Val Gly Leu Ser Val Asp Phe Thr Val Asn Tyr
865                 870                 875                 880

Cys Ile Ser Tyr His Leu Cys Pro His Pro Asp Arg Leu Ser Arg Val
                885                 890                 895

Ala Phe Ser Leu Arg Gln Thr Ser Cys Ala Thr Ala Val Gly Ala Ala
            900                 905                 910

Ala Leu Phe Ala Ala Gly Val Leu Met Leu Pro Ala Thr Val Leu Leu
        915                 920                 925

Tyr Arg Lys Leu Gly Ile Ile Leu Met Met Val Lys Cys Val Ser Cys
    930                 935                 940

Gly Phe Ala Ser Phe Phe Phe Gln Ser Leu Cys Cys Phe Phe Gly Pro
945                 950                 955                 960

Glu Lys Asn Cys Gly Gln Ile Leu Trp Pro Cys Ala His Leu Pro Trp
                965                 970                 975

Asp Ala Gly Thr Gly Asp Pro Gly Gly Glu Lys Ala Gly Arg Pro Arg
            980                 985                 990

Pro Gly Ser Val Gly Gly Met Pro  Gly Ser Cys Ser Glu  Gln Tyr Glu
        995                 1000                1005

Leu Gln  Pro Leu Ala Arg Arg  Arg Ser Pro Ser Phe  Asp Thr Ser
    1010                1015                1020

Thr Ala  Thr Ser Lys Leu Ser  His Arg Pro Ser Val  Leu Ser Glu
    1025                1030                1035

Asp Leu  Gln Leu His Asp Gly  Pro Cys Cys Ser Arg  Pro Pro Pro
    1040                1045                1050

Ala Pro  Ala Ser Pro Arg Glu  Leu Leu Leu Asp His  Gln Ala Val
    1055                1060                1065

Phe Ser  Gln Cys Pro Ala Leu  Gln Thr Ser Ser Pro  Tyr Lys Gln
    1070                1075                1080

Ala Gly  Pro Ser Pro Lys Thr  Arg Ala Arg Gln Asp  Ser Gln Gly
    1085                1090                1095

Glu Glu  Ala Glu Pro Leu Pro  Ala Ser Pro Glu Ala  Pro Ala His
    1100                1105                1110

Ser Pro  Lys Ala Lys Ala Ala  Asp Pro Pro Asp Gly  Phe Cys Ser
    1115                1120                1125

Ser Ala  Ser Thr Leu Glu Gly  Leu Ser Val Ser Asp  Glu Thr Cys
    1130                1135                1140

Leu Ser  Thr Ser Glu Pro Ser  Ala Arg Val Pro Asp  Ser Val Gly
    1145                1150                1155

Val Ser  Pro Asp Asp Leu Asp  Asp Thr Gly Gln Pro  Val Leu Glu
    1160                1165                1170

Arg Gly  Gln Leu Asn Gly Lys  Arg Asp Thr Leu Trp  Leu Ala Leu
    1175                1180                1185

Arg Glu  Thr Val Tyr Asp Pro  Ser Leu Pro Ala Ser  His His Ser
    1190                1195                1200

Ser Leu  Ser Trp Lys Gly Arg  Gly Gly Pro Gly Asp  Gly Ser Pro
    1205                1210                1215

Val Val  Leu Pro Asn Ser Gln  Pro Asp Leu Pro Asp  Val Trp Leu
    1220                1225                1230

Arg Arg  Pro Ser Thr His Thr  Ser Gly Tyr Ser Ser
    1235                1240                1245
```

<210> SEQ ID NO 19

<211> LENGTH: 1492
<212> TYPE: PRT
<213> ORGANISM: Homo sapiens
<220> FEATURE:
<221> NAME/KEY: MISC_FEATURE
<223> OTHER INFORMATION: Amino acid sequence of SEQ ID NO: 2

<400> SEQUENCE: 19

```
Met Gly Arg Lys Thr Gln Pro Asp Ala Ser Pro His Trp Gly Gly Glu
1               5                   10                  15

Glu Gly Ala Glu Arg Ala Gly Asn Leu Ala Gly Leu Lys Pro Pro Ala
            20                  25                  30

Ser Thr Arg Gly Val Gln Arg Gly Glu Val Arg Ala Trp Ser Ser Pro
        35                  40                  45

Ser Ile Arg Leu Glu Gly Ala Tyr Ala Cys Ala Arg Ala Pro Arg Arg
    50                  55                  60

Arg Cys Arg Arg His Arg Arg Arg Arg Arg Arg Arg Arg Gly Phe Ser
65                  70                  75                  80

Thr Ser Ala Arg Thr Ala Val Pro Pro Thr Gly Met Asp Gly Asp Ser
                85                  90                  95

Ser Ser Ser Ser Gly Gly Ser Gly Pro Ala Pro Gly Pro Gly Pro Glu
            100                 105                 110

Gly Glu Gln Arg Pro Glu Gly Glu Pro Leu Ala Pro Asp Gly Gly Ser
        115                 120                 125

Pro Asp Ser Thr Gln Thr Lys Ala Val Pro Pro Glu Ala Ser Pro Glu
    130                 135                 140

Arg Ser Cys Ser Leu His Ser Cys Pro Leu Glu Asp Pro Ser Ser Ser
145                 150                 155                 160

Ser Gly Pro Pro Pro Thr Thr Ser Thr Leu Gln Pro Val Gly Pro Ser
                165                 170                 175

Ser Pro Leu Ala Pro Ala His Phe Thr Tyr Pro Arg Ala Leu Gln Glu
            180                 185                 190

Tyr Gln Gly Gly Ser Ser Leu Pro Gly Leu Gly Asp Arg Ala Ala Leu
        195                 200                 205

Cys Ser His Gly Ser Ser Leu Ser Pro Ser Pro Ala Pro Ser Gln Arg
    210                 215                 220

Asp Gly Thr Trp Lys Pro Pro Ala Val Gln His His Val Val Ser Val
225                 230                 235                 240

Arg Gln Glu Arg Ala Phe Gln Met Pro Lys Ser Tyr Ser Gln Leu Ile
                245                 250                 255

Ala Glu Trp Pro Val Ala Val Leu Met Leu Cys Leu Ala Val Ile Phe
            260                 265                 270

Leu Cys Thr Leu Ala Gly Leu Leu Gly Ala Arg Leu Pro Asp Phe Ser
        275                 280                 285

Lys Pro Leu Leu Gly Phe Glu Pro Arg Asp Thr Asp Ile Gly Ser Lys
    290                 295                 300

Leu Val Val Trp Arg Ala Leu Gln Ala Leu Thr Gly Pro Arg Lys Leu
305                 310                 315                 320

Leu Phe Leu Ser Pro Asp Leu Glu Leu Asn Ser Ser Ser Ser His Asn
                325                 330                 335

Thr Leu Arg Pro Ala Pro Arg Gly Ser Ala Gln Glu Ser Ala Val Arg
            340                 345                 350

Pro Arg Arg Met Val Glu Pro Leu Glu Asp Arg Arg Gln Glu Asn Phe
        355                 360                 365

Phe Cys Gly Pro Pro Glu Lys Ser Tyr Ala Lys Leu Val Phe Met Ser
    370                 375                 380
```

```
Thr Ser Ser Gly Ser Leu Trp Asn Leu His Ala Ile His Ser Met Cys
385                 390                 395                 400

Arg Met Glu Gln Asp Gln Ile Arg Ser His Thr Ser Phe Gly Ala Leu
                405                 410                 415

Cys Gln Arg Thr Ala Ala Asn Gln Cys Cys Pro Ser Trp Ser Leu Gly
            420                 425                 430

Asn Tyr Leu Ala Val Leu Ser Asn Arg Ser Ser Cys Leu Asp Thr Thr
        435                 440                 445

Gln Ala Asp Ala Ala Arg Thr Leu Ala Leu Leu Arg Thr Cys Ala Leu
    450                 455                 460

Tyr Tyr His Ser Gly Ala Leu Val Pro Ser Cys Leu Gly Pro Gly Gln
465                 470                 475                 480

Asn Lys Ser Pro Arg Cys Ala Gln Val Pro Thr Lys Cys Ser Gln Ser
                485                 490                 495

Ser Ala Ile Tyr Gln Leu Leu His Phe Leu Leu Asp Arg Asp Phe Leu
            500                 505                 510

Ser Pro Gln Thr Thr Asp Tyr Gln Val Pro Ser Leu Lys Tyr Ser Leu
        515                 520                 525

Leu Phe Leu Pro Thr Pro Lys Gly Ala Ser Leu Met Asp Ile Tyr Leu
    530                 535                 540

Asp Arg Leu Ala Thr Pro Trp Gly Leu Ala Asp Asn Tyr Thr Ser Val
545                 550                 555                 560

Thr Gly Met Asp Leu Gly Leu Lys Gln Glu Leu Leu Arg His Phe Leu
                565                 570                 575

Val Gln Asp Thr Val Tyr Pro Leu Leu Ala Leu Val Ala Ile Phe Phe
            580                 585                 590

Gly Met Ala Leu Tyr Leu Arg Ser Leu Phe Leu Thr Leu Met Val Leu
        595                 600                 605

Leu Gly Val Leu Gly Ser Leu Leu Val Ala Phe Phe Leu Tyr Gln Val
    610                 615                 620

Ala Phe Arg Met Ala Tyr Phe Pro Phe Val Asn Leu Ala Ala Leu Leu
625                 630                 635                 640

Leu Leu Ser Ser Val Cys Ala Asn His Thr Leu Ile Phe Phe Asp Leu
                645                 650                 655

Trp Arg Leu Ser Lys Ser Gln Leu Pro Ser Gly Gly Leu Ala Gln Arg
            660                 665                 670

Val Gly Arg Thr Met His His Phe Gly Tyr Leu Leu Leu Val Ser Gly
        675                 680                 685

Leu Thr Thr Ser Ala Ala Phe Tyr Ala Ser Tyr Leu Ser Arg Leu Pro
    690                 695                 700

Ala Val Arg Cys Leu Ala Leu Phe Met Gly Thr Ala Val Leu Val His
705                 710                 715                 720

Leu Ala Leu Thr Leu Val Trp Leu Pro Ala Ser Ala Val Leu His Glu
                725                 730                 735

Arg Tyr Leu Ala Arg Gly Cys Ala Arg Arg Ala Arg Gly Arg Trp Glu
            740                 745                 750

Gly Ser Ala Pro Arg Arg Leu Leu Leu Ala Leu His Arg Arg Leu Arg
        755                 760                 765

Gly Leu Arg Arg Ala Ala Ala Gly Thr Ser Arg Leu Leu Phe Gln Arg
    770                 775                 780

Leu Leu Pro Cys Gly Val Ile Lys Phe Arg Tyr Ile Trp Ile Cys Trp
785                 790                 795                 800

Phe Ala Ala Leu Ala Ala Gly Gly Ala Tyr Ile Ala Gly Val Ser Pro
```

```
                805                 810                 815

Arg Leu Arg Leu Pro Thr Leu Pro Pro Pro Gly Gly Gln Val Phe Arg
            820                 825                 830

Pro Ser His Pro Phe Glu Arg Phe Asp Ala Glu Tyr Arg Gln Leu Phe
        835                 840                 845

Leu Phe Glu Gln Leu Pro Gln Gly Glu Gly Gly His Met Pro Val Val
    850                 855                 860

Leu Val Trp Gly Val Leu Pro Val Asp Thr Gly Asp Pro Leu Asp Pro
865                 870                 875                 880

Arg Ser Asn Ser Ser Leu Val Arg Asp Pro Ala Phe Ser Ala Ser Gly
                885                 890                 895

Pro Glu Ala Gln Arg Trp Leu Leu Ala Leu Cys His Arg Ala Arg Asn
            900                 905                 910

Gln Ser Phe Phe Asp Thr Leu Gln Glu Gly Trp Pro Thr Leu Cys Phe
        915                 920                 925

Val Glu Thr Leu Gln Arg Trp Met Glu Ser Pro Ser Cys Ala Arg Leu
    930                 935                 940

Gly Pro Asp Leu Cys Cys Gly His Ser Asp Phe Pro Trp Ala Pro Gln
945                 950                 955                 960

Phe Phe Leu His Cys Leu Lys Met Met Ala Leu Glu Gln Gly Pro Asp
                965                 970                 975

Gly Thr Gln Asp Leu Gly Leu Arg Phe Asp Ala His Gly Ser Leu Ala
            980                 985                 990

Ala Leu Val Leu Gln Phe Gln Thr  Asn Phe Arg Asn Ser  Pro Asp Tyr
        995                 1000                1005

Asn Gln  Thr Gln Leu Phe Tyr  Asn Glu Val Ser His  Trp Leu Ala
    1010                 1015                 1020

Ala Glu  Leu Gly Met Ala Pro  Pro Gly Leu Arg Arg  Gly Trp Phe
    1025                 1030                 1035

Thr Ser  Arg Leu Glu Leu Tyr  Ser Leu Gln His Ser  Leu Ser Thr
    1040                 1045                 1050

Glu Pro  Ala Val Val Leu Gly  Leu Ala Leu Ala Leu  Ala Phe Ala
    1055                 1060                 1065

Thr Leu  Leu Leu Gly Thr Trp  Asn Val Pro Leu Ser  Leu Phe Ser
    1070                 1075                 1080

Val Ala  Ala Val Ala Gly Thr  Val Leu Leu Thr Val  Gly Leu Leu
    1085                 1090                 1095

Val Leu  Leu Glu Trp Gln Leu  Asn Thr Ala Glu Ala  Leu Phe Leu
    1100                 1105                 1110

Ser Ala  Ser Val Gly Leu Ser  Val Asp Phe Thr Val  Asn Tyr Cys
    1115                 1120                 1125

Ile Ser  Tyr His Leu Cys Pro  His Pro Asp Arg Leu  Ser Arg Val
    1130                 1135                 1140

Ala Phe  Ser Leu Arg Gln Thr  Ser Cys Ala Thr Ala  Val Gly Ala
    1145                 1150                 1155

Ala Ala  Leu Phe Ala Ala Gly  Val Leu Met Leu Pro  Ala Thr Val
    1160                 1165                 1170

Leu Leu  Tyr Arg Lys Leu Gly  Ile Ile Leu Met Met  Val Lys Cys
    1175                 1180                 1185

Val Ser  Cys Gly Phe Ala Ser  Phe Phe Phe Gln Ser  Leu Cys Cys
    1190                 1195                 1200

Phe Phe  Gly Pro Glu Lys Asn  Cys Gly Gln Ile Leu  Trp Pro Cys
    1205                 1210                 1215
```

```
Ala His  Leu Pro Trp Asp Ala  Gly Thr Gly Asp Pro  Gly Gly Glu
    1220                 1225                 1230

Lys Ala  Gly Arg Pro Arg Pro  Gly Ser Val Gly Gly  Met Pro Gly
    1235                 1240                 1245

Ser Cys  Ser Glu Gln Tyr Glu  Leu Gln Pro Leu Ala  Arg Arg Arg
    1250                 1255                 1260

Ser Pro  Ser Phe Asp Thr Ser  Thr Ala Thr Ser Lys  Leu Ser His
    1265                 1270                 1275

Arg Pro  Ser Val Leu Ser Glu  Asp Leu Gln Leu His  Asp Gly Pro
    1280                 1285                 1290

Cys Cys  Ser Arg Pro Pro Pro  Ala Pro Ala Ser Pro  Arg Glu Leu
    1295                 1300                 1305

Leu Leu  Asp His Gln Ala Val  Phe Ser Gln Cys Pro  Ala Leu Gln
    1310                 1315                 1320

Thr Ser  Ser Pro Tyr Lys Gln  Ala Gly Pro Ser Pro  Lys Thr Arg
    1325                 1330                 1335

Ala Arg  Gln Asp Ser Gln Gly  Glu Glu Ala Glu Pro  Leu Pro Ala
    1340                 1345                 1350

Ser Pro  Glu Ala Pro Ala His  Ser Pro Lys Ala Lys  Ala Ala Asp
    1355                 1360                 1365

Pro Pro  Asp Gly Phe Cys Ser  Ser Ala Ser Thr Leu  Glu Gly Leu
    1370                 1375                 1380

Ser Val  Ser Asp Glu Thr Cys  Leu Ser Thr Ser Glu  Pro Ser Ala
    1385                 1390                 1395

Arg Val  Pro Asp Ser Val Gly  Val Ser Pro Asp Asp  Leu Asp Asp
    1400                 1405                 1410

Thr Gly  Gln Pro Val Leu Glu  Arg Gly Gln Leu Asn  Gly Lys Arg
    1415                 1420                 1425

Asp Thr  Leu Trp Leu Ala Leu  Arg Glu Thr Val Tyr  Asp Pro Ser
    1430                 1435                 1440

Leu Pro  Ala Ser His His Ser  Ser Leu Ser Trp Lys  Gly Arg Gly
    1445                 1450                 1455

Gly Pro  Gly Asp Gly Ser Pro  Val Val Leu Pro Asn  Ser Gln Pro
    1460                 1465                 1470

Asp Leu  Pro Asp Val Trp Leu  Arg Arg Pro Ser Thr  His Thr Ser
    1475                 1480                 1485

Gly Tyr  Ser Ser
    1490


<210> SEQ ID NO 20
<211> LENGTH: 1245
<212> TYPE: PRT
<213> ORGANISM: Homo sapiens
<220> FEATURE:
<221> NAME/KEY: misc_feature
<223> OTHER INFORMATION: Consensus sequence of pj01304GS and pj01034s1
      sequences

<400> SEQUENCE: 20

Met Pro Lys Ser Tyr Ser Gln Leu Ile Ala Glu Trp Pro Val Ala Val
1               5                   10                  15

Leu Met Leu Cys Leu Ala Val Ile Phe Leu Cys Thr Leu Ala Gly Leu
            20                  25                  30

Leu Gly Ala Arg Leu Pro Asp Phe Ser Lys Pro Leu Leu Gly Phe Glu
        35                  40                  45

Pro Arg Asp Thr Asp Ile Gly Ser Lys Leu Val Val Trp Arg Ala Leu
    50                  55                  60
```

-continued

```
Gln Ala Leu Thr Gly Pro Arg Lys Leu Leu Phe Leu Ser Pro Asp Leu
65                  70                  75                  80

Glu Leu Asn Ser Ser Ser Ser His Asn Thr Leu Arg Pro Ala Pro Arg
                85                  90                  95

Gly Ser Ala Gln Glu Ser Ala Val Arg Pro Arg Arg Met Val Glu Pro
            100                 105                 110

Leu Glu Asp Arg Arg Gln Glu Asn Phe Phe Cys Gly Pro Pro Glu Lys
        115                 120                 125

Ser Tyr Ala Lys Leu Val Phe Met Ser Thr Ser Ser Gly Ser Leu Trp
    130                 135                 140

Asn Leu His Ala Ile His Ser Met Cys Arg Met Glu Gln Asp Gln Ile
145                 150                 155                 160

Arg Ser His Thr Ser Phe Gly Ala Leu Cys Gln Arg Thr Ala Ala Asn
                165                 170                 175

Gln Cys Cys Pro Ser Trp Ser Leu Gly Asn Tyr Leu Ala Val Leu Ser
            180                 185                 190

Asn Arg Ser Ser Cys Leu Asp Thr Thr Gln Ala Asp Ala Ala Arg Thr
        195                 200                 205

Leu Ala Leu Leu Arg Thr Cys Ala Leu Tyr Tyr His Ser Gly Ala Leu
    210                 215                 220

Val Pro Ser Cys Leu Gly Pro Gly Gln Asn Lys Ser Pro Arg Cys Ala
225                 230                 235                 240

Gln Val Pro Thr Lys Cys Ser Gln Ser Ser Ala Ile Tyr Gln Leu Leu
                245                 250                 255

His Phe Leu Leu Asp Arg Asp Phe Leu Ser Pro Gln Thr Thr Asp Tyr
            260                 265                 270

Gln Val Pro Ser Leu Lys Tyr Ser Leu Leu Phe Leu Pro Thr Pro Lys
        275                 280                 285

Gly Ala Ser Leu Met Asp Ile Tyr Leu Asp Arg Leu Ala Thr Pro Trp
    290                 295                 300

Gly Leu Ala Asp Asn Tyr Thr Ser Val Thr Gly Met Asp Leu Gly Leu
305                 310                 315                 320

Lys Gln Glu Leu Leu Arg His Phe Leu Val Gln Asp Thr Val Tyr Pro
                325                 330                 335

Leu Leu Ala Leu Val Ala Ile Phe Phe Gly Met Ala Leu Tyr Leu Arg
            340                 345                 350

Ser Leu Phe Leu Thr Leu Met Val Leu Leu Gly Val Leu Gly Ser Leu
        355                 360                 365

Leu Val Ala Phe Phe Leu Tyr Gln Val Ala Phe Arg Met Ala Tyr Phe
    370                 375                 380

Pro Phe Val Asn Leu Ala Ala Leu Leu Leu Leu Ser Ser Val Cys Ala
385                 390                 395                 400

Asn His Thr Leu Ile Phe Phe Asp Leu Trp Arg Leu Ser Lys Ser Gln
                405                 410                 415

Leu Pro Ser Gly Gly Leu Ala Gln Arg Val Gly Arg Thr Met His His
            420                 425                 430

Phe Gly Tyr Leu Leu Leu Val Ser Gly Leu Thr Thr Ser Ala Ala Phe
        435                 440                 445

Tyr Ala Ser Tyr Leu Ser Arg Leu Pro Ala Val Arg Cys Leu Ala Leu
    450                 455                 460

Phe Met Gly Thr Ala Val Leu Val His Leu Ala Leu Thr Leu Val Trp
465                 470                 475                 480

Leu Pro Ala Ser Ala Val Leu His Glu Arg Tyr Leu Ala Arg Gly Cys
```

-continued

```
                485                 490                 495

Ala Arg Arg Ala Arg Gly Arg Trp Glu Gly Ser Ala Pro Arg Arg Leu
            500                 505                 510

Leu Leu Ala Leu His Arg Arg Leu Arg Gly Leu Arg Arg Ala Ala Ala
        515                 520                 525

Gly Thr Ser Arg Leu Leu Phe Gln Arg Leu Leu Pro Cys Gly Val Ile
    530                 535                 540

Lys Phe Arg Tyr Ile Trp Ile Cys Trp Phe Ala Ala Leu Ala Ala Gly
545                 550                 555                 560

Gly Ala Tyr Ile Ala Gly Val Ser Pro Arg Leu Arg Leu Pro Thr Leu
                565                 570                 575

Pro Pro Pro Gly Gly Gln Val Phe Arg Pro Ser His Pro Phe Glu Arg
            580                 585                 590

Phe Asp Ala Glu Tyr Arg Gln Leu Phe Leu Phe Glu Gln Leu Pro Gln
        595                 600                 605

Gly Glu Gly Gly His Met Pro Val Val Leu Val Trp Gly Val Leu Pro
    610                 615                 620

Val Asp Thr Gly Asp Pro Leu Asp Pro Arg Ser Asn Ser Ser Leu Val
625                 630                 635                 640

Arg Asp Pro Ala Phe Ser Ala Ser Gly Pro Glu Ala Gln Arg Trp Leu
                645                 650                 655

Leu Ala Leu Cys His Arg Ala Arg Asn Gln Ser Phe Phe Asp Thr Leu
            660                 665                 670

Gln Glu Gly Trp Pro Thr Leu Cys Phe Val Glu Thr Leu Gln Arg Trp
        675                 680                 685

Met Glu Ser Pro Ser Cys Ala Arg Leu Gly Pro Asp Leu Cys Cys Gly
    690                 695                 700

His Ser Asp Phe Pro Trp Ala Pro Gln Phe Phe Leu His Cys Leu Lys
705                 710                 715                 720

Met Met Ala Leu Glu Gln Gly Pro Asp Gly Thr Gln Asp Leu Gly Leu
                725                 730                 735

Arg Phe Asp Ala His Gly Ser Leu Ala Ala Leu Val Leu Gln Phe Gln
            740                 745                 750

Thr Asn Phe Arg Asn Ser Pro Asp Tyr Asn Gln Thr Gln Leu Phe Tyr
        755                 760                 765

Asn Glu Val Ser His Trp Leu Ala Ala Glu Leu Gly Met Ala Pro Pro
    770                 775                 780

Gly Leu Arg Arg Gly Trp Phe Thr Ser Arg Leu Glu Leu Tyr Ser Leu
785                 790                 795                 800

Gln His Ser Leu Ser Thr Glu Pro Ala Val Val Leu Gly Leu Ala Leu
                805                 810                 815

Ala Leu Ala Phe Ala Thr Leu Leu Leu Gly Thr Trp Asn Val Pro Leu
            820                 825                 830

Ser Leu Phe Ser Val Ala Ala Val Ala Gly Thr Val Leu Leu Thr Val
        835                 840                 845

Gly Leu Leu Val Leu Leu Glu Trp Gln Leu Asn Thr Ala Glu Ala Leu
    850                 855                 860

Phe Leu Ser Ala Ser Val Gly Leu Ser Val Asp Phe Thr Val Asn Tyr
865                 870                 875                 880

Cys Ile Ser Tyr His Leu Cys Pro His Pro Asp Arg Leu Ser Arg Val
                885                 890                 895

Ala Phe Ser Leu Arg Gln Thr Ser Cys Ala Thr Ala Val Gly Ala Ala
            900                 905                 910
```

-continued

```
Ala Leu Phe Ala Ala Gly Val Leu Met Leu Pro Ala Thr Val Leu Leu
        915                 920                 925

Tyr Arg Lys Leu Gly Ile Ile Leu Met Met Val Lys Cys Val Ser Cys
    930                 935                 940

Gly Phe Ala Ser Phe Phe Phe Gln Ser Leu Cys Cys Phe Phe Gly Pro
945                 950                 955                 960

Glu Lys Asn Cys Gly Gln Ile Leu Trp Pro Cys Ala His Leu Pro Trp
                965                 970                 975

Asp Ala Gly Thr Gly Asp Pro Gly Gly Glu Lys Ala Gly Arg Pro Arg
            980                 985                 990

Pro Gly Ser Val Gly Gly Met Pro  Gly Ser Cys Ser Glu  Gln Tyr Glu
        995                 1000                1005

Leu Gln  Pro Leu Ala Arg Arg  Arg Ser Pro Ser Phe  Asp Thr Ser
    1010                 1015                 1020

Thr Ala  Thr Ser Lys Leu Ser  His Arg Pro Ser Val  Leu Ser Glu
    1025                 1030                 1035

Asp Leu  Gln Leu His Asp Gly  Pro Cys Cys Ser Arg  Pro Pro Pro
    1040                 1045                 1050

Ala Pro  Ala Ser Pro Arg Glu  Leu Leu Leu Asp His  Gln Ala Val
    1055                 1060                 1065

Phe Ser  Gln Cys Pro Ala Leu  Gln Thr Ser Ser Pro  Tyr Lys Gln
    1070                 1075                 1080

Ala Gly  Pro Ser Pro Lys Thr  Arg Ala Arg Gln Asp  Ser Gln Gly
    1085                 1090                 1095

Glu Glu  Ala Glu Pro Leu Pro  Ala Ser Pro Glu Ala  Pro Ala His
    1100                 1105                 1110

Ser Pro  Lys Ala Lys Ala Ala  Asp Pro Pro Asp Gly  Phe Cys Ser
    1115                 1120                 1125

Ser Ala  Ser Thr Leu Glu Gly  Leu Ser Val Ser Asp  Glu Thr Cys
    1130                 1135                 1140

Leu Ser  Thr Ser Glu Pro Ser  Ala Arg Val Pro Asp  Ser Val Gly
    1145                 1150                 1155

Val Ser  Pro Asp Asp Leu Asp  Asp Thr Gly Gln Pro  Val Leu Glu
    1160                 1165                 1170

Arg Gly  Gln Leu Asn Gly Lys  Arg Asp Thr Leu Trp  Leu Ala Leu
    1175                 1180                 1185

Arg Glu  Thr Val Tyr Asp Pro  Ser Leu Pro Ala Ser  His His Ser
    1190                 1195                 1200

Ser Leu  Ser Trp Lys Gly Arg  Gly Gly Pro Gly Asp  Gly Ser Pro
    1205                 1210                 1215

Val Val  Leu Pro Asn Ser Gln  Pro Asp Leu Pro Asp  Val Trp Leu
    1220                 1225                 1230

Arg Arg  Pro Ser Thr His Thr  Ser Gly Tyr Ser Ser
    1235                 1240                 1245


<210> SEQ ID NO 21
<211> LENGTH: 20
<212> TYPE: DNA
<213> ORGANISM: Artificial Sequence
<220> FEATURE:
<223> OTHER INFORMATION: Sythetic primer

<400> SEQUENCE: 21

caagtcctgg cagggaactg                                                  20
```

CANCER-ASSOCIATED GENES

CROSS REFERENCE TO RELATED APPLICATIONS

This application is a Divisional of U.S. application Ser. No. 10/451,000, filed on Sep. 8, 2003, which issued May 20, 2008, as U.S. Pat. No. 7,375,199, which is the national phase of PCT/JP01/11305 filed on Dec. 21, 2001, which designated the United States and which claims priority to Japanese Application 2000-389742 filed on Dec. 22, 2000. The entire contents of the above applications and patent are hereby incorporated by reference.

FIELD OF THE INVENTION

The present invention is related to a novel DNA and a cancer-associated gene comprising the DNA, a recombinant protein encoded by the DNA, an antibody binding to the protein, an anti-cancer agent comprising the antibody, a method of screening a substance that binds to the protein or a peptide fragment thereof.

BACKGROUND OF THE INVENTION

A grand scale sequencing in the Human Genome Project has been producing a lot of information on the nucleotide sequences of human genome every day.

A final goal of the project is not only to determine the whole genomic nucleotide sequences, but also to reveal and understand various human life phenomena based on the information about their structure, i.e., DNA sequence information.

Regions encoding proteins occupy only a small part of the human genome. Although the coding region may recently be predicted by utilizing techniques in information technology such as neural network and hidden markov model, their predictive accuracy is not yet enough.

The present inventors have succeeded in directly cloning a novel DNA comprising a region encoding a protein from cDNA library derived from human adult whole brain, human amygdala, human adult hippocampus, and human fetal whole brain, and in determining its nucleotide sequence, and have completed the present invention.

SUMMARY OF THE INVENTION

A first aspect of the present invention relates to a DNA comprising a nucleotide sequence encoding the following polypeptide (a) or (b):

(a) a polypeptide consisting of an amino acid sequence which is identical or substantially identical with an amino acid sequence represented by SEQ ID No.1 or No.2, (b) a polypeptide consisting of an amino acid sequence represented by SEQ ID No.1 or No.2 in which part of amino acids are deleted, substituted or added, and having substantially the same biological activity as the function of the polypeptide (a).

A second aspect of the present invention relates to a DNA of the following (a) or (b):

(a) a DNA comprising a nucleotide sequence encoding an amino acid sequence represented by SEQ ID No.1 or No.2 in a nucleotide sequence represented by SEQ ID No.1 or No.2, (b) a DNA hybridizing with the DNA (a) under stringent conditions and encoding a protein having substantially the same biological activity as the function of the polypeptide consisting of the amino acid sequence in (a).

The DNAs of the first and second aspects will be also referred to as "the present DNA" in the present specification. The present invention also relates to the gene comprising the present DNAs.

A third aspect of the present invention relates to a protein comprising the following polypeptide (a) or (b):

(a) a polypeptide consisting of an amino acid sequence which is identical or substantially identical with an amino acid sequence represented by SEQ ID No.1 or No.2, (b) a polypeptide consisting of an amino acid sequence represented by SEQ ID No.1 or No.2 in which part of amino acids are deleted, substituted or added, and having substantially the same biological activity as the function of the polypeptide (a), and to a recombinant protein which is obtained by the expression of the gene of the present invention.

A fourth aspect of the present invention relates to various kinds of antibodies binding to the above protein.

A fifth aspect of the present invention relates to various kinds of anti-cancer agents comprising the above antibody.

A sixth aspect of the present invention relates to a method of screening a substance which binds to the above protein or a partial peptide thereof, comprising:

(a) bringing a sample to be tested in contact with said protein or partial peptide thereof, (b) detecting a binding activity between the sample and said protein or partial peptide thereof, and (c) selecting a substance which has a binding activity to said protein or partial peptide thereof.

The seventh aspect of the present invention relates to a polynucleotide hybridizing with the DNA of claim 1 or 2 under the stringent conditions and consisting of at least 15 bases.

The eighth aspect of the present invention relates to a method of detecting cancer with the use of the above polynucleotide as a probe, comprising:

(a) bringing a sample to be tested in contact with said polynucleotide, and (b) detecting a hybridizing activity between the sample and said polynucleotide.

BRIEF DESCRIPTION OF THE DRAWINGS

FIG. 1 shows the presence of two large extracellular domains.

BEST MODE FOR CARRYING OUT THE INVENTION

DNA According to the Present Invention

Figure 1:
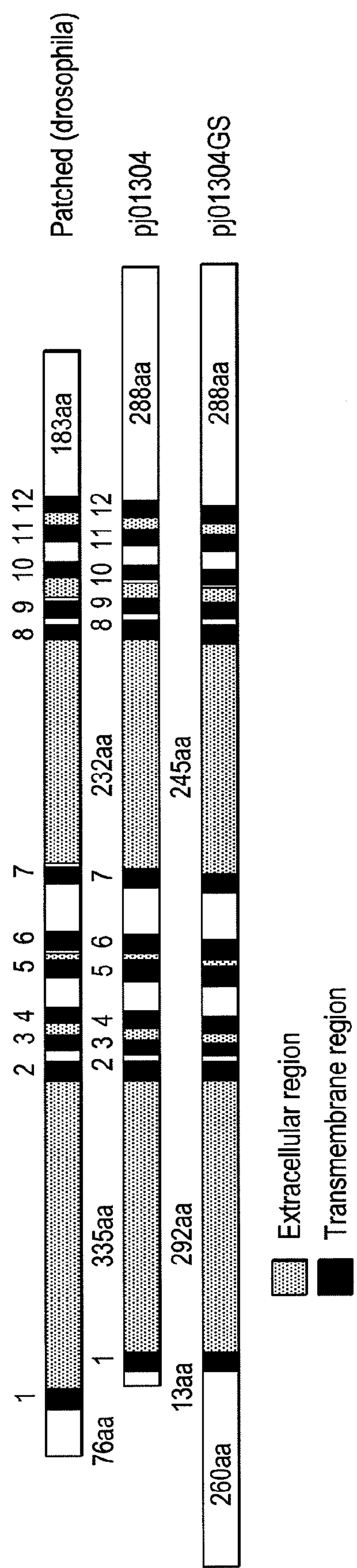
FIG. 1 schematically shows the structures of the proteins of the present invention, "pj01304s1" and "pj01304GS", and Patched protein of *Drosophila*. A transmembrane region is painted in black, and an extracellular region is represented in thin dark.

The present DNA is isolated as cDNA fragment from a cDNA library prepared by the present inventors by using as starting materials mRNAs of human adult whole brain, human amygdala, human adult hippocampus, and human fetal whole brain, are commercially available from Clontech, and identified with determination of its nucleotide sequence.

Thus, clones are randomly isolated from the library derived from human adult whole brain, human amygdala, human adult hippocampus, and human fetal whole brain, which is prepared in accordance with Ohara et al., DNA Research Vol. 4, 53-59 (1997).

Next, after removing overlapped clones (clones which will repeatedly appear) with hybridization, the remaining clones are then subjected to transcription and translation in vitro and nucleotide sequences at both ends of clones which express a product with 50 kDa or more are determined.

Homology search is done on database to remove known genes with the use of the nucleotide sequences at both ends thus obtained as a query. The whole nucleotide sequence is determined for a clone which has identified as a novel gene.

In addition to the above screening method, the 3'- and 5'-terminal sequences are aligned with the human genome. And in the case an unknown long-ORF gene is found in a region caught between them, the whole length analysis of cDNA is done for the gene.

Unknown genes, which could not be obtained by conventional cloning techniques depending on known ones, can now be systematically cloned in this way.

Paying much attention not to make any artificial errors in short fragments or determined sequences, the whole region of human genes comprising the present DNA may be prepared by using PCR methods such as RACE.

A clone (KIAA1742) comprising the present DNA may be obtained accordingly. The function, etc. of a protein encoded by a gene in the clone is disclosed in the present specification.

The present DNA may be alternatively cloned by preparing a synthetic DNA primer with an appropriate nucleotide sequence such as a part of the polypeptide of the present invention, and amplifying it with an appropriate library by means of PCR. The present DNA may be further selected from DNAs integrated into appropriate vectors by means of hybridization with a DNA fragment or synthetic DNA encoding the whole region or part of the present polypeptide.

Hybridization may be performed in accordance with a method described in, for example, current protocols in molecular biology (edited by Frederick M. Ausubel et al., 1987). If a commercial library is used it may be done according to a method described in instructions attached thereto.

The present DNA may be any DNA as long as it consists of a nucleotide sequence which encodes the polypeptide of the present invention, including a cDNA identified and isolated from cDNA libraries derived from human brain and other tissues or cells such as heart, lung, liver, spleen, kidney and testis, and a synthetic DNA.

A vector, which is used in the preparation of the libraries, includes bacteriophage, plasmid, cosmido and phagemid. The cDNA may be also amplified by means of Reverse Transcription coupled Polymerase Chain Reaction (RT-PCR) with the use of a total RNA or mRNA fraction prepared from the above tissues or cells.

An "amino acid sequence which is substantially identical with an amino acid sequence represented by SEQ ID No.1 or No.2" means an amino acid sequence having homology on an average of about 70% or more, preferably about 80% or more, more preferably about 90% or more, further more preferably about 95% or more to the whole amino acid sequence represented by SEQ ID No.1 or No.2.

Thus, the polypeptide consisting of the amino acid sequence which is substantially identical with the amino acid sequence represented by SEQ ID No.1 or No.2 includes a polypeptide having the above homology to the amino acid sequence represented by SEQ ID No.1 or No.2 and having substantially the same biological activity (or function) as the function of a polypeptide consisting of the above amino acid sequence. The term "substantially the same" means the activities or functions of the both substances are the same with each other in quality or property.

The present polypeptide includes a polypeptide consisting of the amino acid sequence represented by SEQ ID No.1 or No.2 in which part of amino acids (preferably 1~20, more preferably 1~10, further more preferably a few amino acids) are deleted, substituted or added, and having substantially the same biological activity (or function) as the function of the polypeptide consisting of the amino acid sequence represented by SEQ ID No.1 or No.2.

The DNA encoding the polypeptide consisting of the amino acid sequence which is substantially identical with the amino acid sequence represented by SEQ ID No.1 or No.2, or the polypeptide consisting of the amino acid sequence represented by SEQ ID No.1 or No.2 in which part of amino acids are deleted, substituted or added may be easily prepared by well known methods such as site-specific mutation, genetic homologous recombination, primer extension method and PCR, or any optional combinations thereof.

In order for the polypeptide or protein to have substantially the same biological activity, it is possible to make a substitution among amino acids belonging to the same group (polar, non-polar, hydrophobic, hydrophilic, positive-charged, negative-charged, or aromatic amino acid group) in the amino acids that constitute the present polypeptide. Alternatively, it is desirable to keep amino acids which are included in a functional domain.

Furthermore, the present DNA includes the DNA comprising a nucleotide sequence encoding the amino acid sequence represented by SEQ ID No.1 or No.2 in the nucleotide sequence represented by SEQ ID No.1 or No.2, and the DNA hybridizing with said DNA under stringent conditions and having substantially the same biological activity as the function of the polypeptide consisting of the amino acid sequence represented by SEQ ID No.1 or No.2.

The DNA that hybridizes with the DNA comprising the nucleotide sequence encoding the amino acid sequence represented by SEQ ID No.1 or No.2 in the nucleotide sequence represented by SEQ ID No.1 or No.2 under stringent conditions includes a DNA having homology on an average of about 80% or more, preferably about 90% or more, more preferably about 95% or more to the whole nucleotide sequence represented by SEQ ID No.1 or No.2.

Hybridization may be performed in accordance with a method described in, for example, current protocols in molecular biology (edited by Frederick M. Ausubel et al., 1987). If a commercial library is used it may be done according to a method described in instructions attached thereto.

The phrase "stringent conditions" in this specification means conditions under which Southern blot hybridization is carried out in an aqueous solution containing 1 mM NaEDTA, 0.5 M $Na_2HPO_4$ (pH 7.2) and 7% SDS at 65° C., followed by the washing of a membrane with an aqueous solution containing 1 mM NaEDTA, 40 mM $Na_2HPO_4$ (pH 7.2) and 1% SDS at 65° C.

The present DNA thus cloned may be directly used, or optionally digested with a restriction enzyme or tagged with a linker for use. The present DNA may have a translation initiation codon "ATG" at its 5'-end, and a translation termination codon, "TAA", "TGA" or "TAG" at its 3' end. These codons may be also added by using an appropriate synthetic DNA adapter.

[Polynucleotide According to the Present Invention]

Since the present DNA (gene) is highly expressed in cancer cells as seen from the following examples, detection of cancer can be done by detecting the gene according to the present invention.

Accordingly, the polynucleotide which hybridizes with the DNA comprising the nucleotide sequence represented by SEQ ID No.1 or No.2 under stringent conditions may be used as probe in the above detection of cancer.

The length of the polynucleotide is at least 15 bases, preferably 100 bases or more, more preferably 500 bases or more, further more preferably 1,000 bases or more.

The phrase "stringent conditions" in this specification means conditions under which Southern blot hybridization is carried out in an aqueous solution containing 1 mM NaEDTA, 0.5M $Na_2HPO_4$ (pH 7.2) and 7% SDS at 65° C., followed by the washing of a membrane with an aqueous solution containing 1 mM NaEDTA, 40 mM $Na_2HPO_4$ (pH 7.2) and 1% SDS at 65° C.

[Protein According to the Present Invention]

The protein according to the present invention may be easily prepared by any method known to those skilled in the art, by constructing an expression vector comprising the present DNA or the gene comprising thereof, culturing a transformant transformed with the expression vector to produce and accumulate the present polypeptide or a recombinant protein comprising thereof, and collecting them.

The expression vector may be constructed by any known method in the art. For example, it is made by (1) excising a DNA fragment containing the present DNA or the gene comprising the DNA, and (2) ligating the DNA fragment downstream of a promoter in the expression vector.

Vectors to be used in the present invention include those derived from *Escherichia coli* such as pBR322, pBR325, pUC18, pUC118; those derived from *Bacillus subtilis* such as pUB110, pTP5 and pC194; those derived from yeast such as pSH19 and pSH15; bacteriophage such as λphage; animal viruses such as retorovirus, vaccinia virus and baculovirus.

Promoters to be used in the present invention may be any promoters suitable for a host cell which is used in the expression of the gene, including, for example, trp promoter, lac promoter, recA promoter, λPL promoter and lpp promoter for *E. coli*; SPO1 promoter, SPO2 promoter and penP promoter for *Bacillus subtilis*; PHO5 promoter, PGK promoter, GAP promoter and ADH promoter for yeast; and SRα promoter, SV40 promoter, LTR promoter, CMV promoter and HSV-TK promoter for animal cells.

Other elements known in the art such as an enhancer, a splicing signal, a polyadenylation signal, a selection marker and SV40 replication origin may be added to the expression vectors. The protein encoded by the present DNA may be optionally expressed as a fused protein with other proteins such as glutathione-S-transferase and protein A. The fused protein may be cleaved by an appropriate protease and separated into each protein.

The host cell used in the present invention includes *Escherichia, Bacillus*, yeast, insect cells, and animal cells.

The examples of *Escherichia* include *E. coli* K-12 DH1 (Proc. Natl. Acad, Sci., USA, vol. 60 160 (1968)), JM103 (Nucleic Acids Research, vol. 9, 309 (1981)), JA221 (Journal of Molecular Biology, vol. 120, 517 (1978)) and HB101 (Journal of Molecular Biology, vol. 41, 459 (1969)).

The examples of *Bacillus* include *Bacillus subtilis* MI114 (Gene vol. 24, 255 (1983)), and 207-21 (Journal of Molecular Biology, vol. 95, 87 (1984)).

The examples of yeast include *Saccaromyces cerevisiae* AH22, AH22R-, NA87-11A, DKD-5D, and 20B-12; *Schizosaccaromyces pombe* NCYC1913, NCYC2036; and *Saccaromyces picjia pastoris.*

The examples of animal cells include simian cell COS-7, Vero, Chinese hamster cell CHO ("CHO cell"), dhfr gene-defective CHO cell, mouse L cell, mouse AtT-20 cell, mouse myeloma cell, rat GH3 cell and human FL cell.

The transformation of these cells may be carried out in accordance with a method known in the art such as those described in the following articles:

Proc. Natl. Acad. Sci., USA vol. 69, 2110 (1972); Gene, vol. 17, 107 (1982), Molecular & General Genetics, vol. 168, 111 (1979); Methods in Enzymology, vol. 194, 182-187 (1991); Proc. Natl. Acad. Sci., USA vol. 75, 1929 (1978); Cell Engineering, additional volume 8, "New Cell Engineering experimental protocols, 263-267 (published by Shu-junn Co.); and Virology vol. 52 456 (1973).

The transformant thus transformed with the expression vector comprising the present DNA or the gene comprising thereof may be cultured according to a method known in the art.

*Escherichia* host cells may be normally cultured at about 15~43° C. for about 3~24 hours with aeration and stirring, if necessary. *Bacillus* host cells may be normally cultured at about 30~40° C. for about 6~24 hours with aeration and stirring, if necessary.

Yeast host cells may be normally cultured in a culture medium with pH about 5~8 at about 20~35° C. for about 24~72 hours with aeration and stirring, if necessary.

Animal host cells may be normally cultured in a culture medium with pH about 6~8 at about 30~40° C. for about 15~60 hours with aeration and stirring, if necessary.

The polypeptide or protein according to the present invention may be isolated and purified from the above culture as follows. After the completion of culturing, bacteria or cells are collected by a known method, suspended in an appropriate buffer solution, and destroyed by means of ultrasonic, lysozyme and/or freezing and thawing treatment, followed by centrifugation or filtration to give a crude protein extract. The buffer solution may contain a protein-denaturing agent such as urea and guanidine hydrochloride, or a surfactant such as TritonX-100™. If the protein is secreted into the culture medium, the bacteria or cells are separated from its supernatant by a known method after the completion of culturing, and the resulting supernatant is collected. The protein thus obtained and contained in the culture supernatant or extract may be purified by an appropriate combination of known separation and purification methods.

The present polypeptide or protein thus obtained may be converted into their salt form, which may be converted into its free from vice versa or into other salt forms according to a known method. The protein produced by the transformant may be treated with an appropriate protein-modifying enzyme such as trypsin or chymotrypsin in order to optionally add modification to it or to partially remove polypeptide from it before or after purification.

The presence of present polypeptide or protein or salt thereof may be determined by various binding assay methods or enzyme immunoassay using a specific antibody.

[Antibody According to the Present Invention]

There is no limitation in the present antibody as long as it binds to the protein according to the present invention. It may be obtained as a polyclonal antibody or monoclonal antibody by a known method. A preferable example of the present antibody is a monoclonal antibody derived from mammalian, which contains the one produced by a hybridoma and the one produced by a host cell which has been transformed by genetic engineering technique with an expression vector comprising a gene encoding the antibody. It is preferable that the present antibody specifically binds to the present protein.

The hybridoma producing the monoclonal antibody may be prepared with the use of a known technique. Thus, it is prepared by doing immunization with the present protein as a sensitizing antigen by a known method, fusing the resulting immunocyte with a known parent cell by a known cell fusion method, and screening a monoclonal antibody-producing cell by a known screening method. More specifically, the monoclonal antibody is prepared as follows.

A gene sequence encoding the present protein is inserted into a known expression vector system and an appropriate host cell is transformed with the vector, followed by purification of a desired protein from the host cell or a culture supernatant.

Next, the resulting protein is used as the sensitizing antigen. Alternatively, a partial polypeptide of the present protein, which may be usually obtained by a chemical synthesis method known to those skilled in the art based on the amino acid sequence of the present protein, is also used as the sensitizing antigen.

The partial polypeptide of the present protein includes those which have at least 10 amino acids or more, preferably at least 50 amino acids or more, more preferably at least 70 amino acids or more, further more preferably at least 100 amino acids or more, most preferably 200 amino acids or more of the amino acid sequence constituting the present protein, and the polypeptide have substantially the same biological activity with the function of the polypeptide according to the present invention. The partial polypeptide preferably comprises a functional domain, which will be described hereinafter. Although the C-end of the partial polypeptide is usually a carboxyl group (—COOH) or a carboxylate group (—COO—), it may be also an amide group (—$CONH_2$) or an ester group (—COOR) as it is for the present protein. The N-end of the partial polypeptide includes the one in which an amino group of methionine is protected with a protecting group, the one having a glutamyl group formed by cutting of the N-end in a body and subjected to pyroglutamic acid oxidation, the one in which a substituted group in the side chain of an amino acid is protected with an appropriate protecting group, and a complex peptide such as a glycopeptide in which a sugar chain is coupled.

The present antibody may be used in the detection and purification, etc. of the present protein Since the present gene is expressed in a high degree in cancer cells as described in the Examples, the present antibody that is coupled with a radio isotope, a chemotherapeutic agent, toxins derived from bacteria can inhibit the growth of the cells. An epitope existing on the present protein, which can be recognized by the present antibody, is not limited to any particular one. Accordingly, any fragment may be used as the antigen in the preparation of the present antibody, as long as it comprises the epitope existing on the present protein.

The animal to be immunized with the sensitizing antigen is not limited to a particular one, but is usually selected in view of compatibility with the parent cell used in the cell fusion, including rodent such as mouse, rat and hamster.

The animal may be immunized with the sensitizing antigen by a known method, usually by intraperitoneal or subcutaneous injection. More specifically, the sensitizing antigen appropriately diluted and suspended in PBS (Phosphate-Buffered Saline) or physiological saline is appropriately mixed with a usual adjuvant such as Freund's complete adjuvant, emulsified and administered to the animal several times at an interval of 4-12 days. An appropriate carrier may be used in the immunization.

After the increase of an antibody level in serum of the immunized animal is confirmed, the immunocyte is collected and subjected to the cell fusion. A preferable immunocyte, for example, is a spleen cell.

The parent cell to be fused with the immunocyte is myeloma derived from mammalian, which includes various known cell strains such as P3 (P3x63Ag8.653) (J. Immunol. (1979) 123, 1548-1550), P3x63Ag8U.1 (Current Topics in Microbiology and Immunology (1978) 81, 1-7), NS-1 (Kohler, G. and Milstein, C. Eur. J. Immunol. (1976) 6, 511-519), MPC-11 (Marguiles, D. H., et al., Cell (1976) 8, 405-415), SP2/0 (Shulman, M. et al., Nature (1978) 276, 269-270), FO (de St., Groth, S. F. et al., J. Immunol. Methods (1980) 35, 1-21), S194 (Trowbridge, I. S. J. Exp. Med. (1978) 148, 313-323), and R210 (Galfre, G et al., Nature (1979) 277, 131-133).

The cell fusion between the immunocyte and myeloma may be done according to a known method such as that in Kohler, G. and Milstein, C. Methods Enzymol. (1981) 73, 3-46.

More specifically, the cell fusion is carried out in a usual nutritional medium in the presence of a cell fusion-promoting agent such as polyethyleneglycol (PEG) and Sendai virus (Hemagglutinating Virus of Japan:HVJ). An auxiliary agent such as dimethylsulfoxide may be optionally supplemented to increase hybridization efficiency.

A ratio of the amount of immunocyte to that of myeloma may be optionally selected, being preferably 1-10. Culture medium to be used in the cell fusion includes any culture medium which is used for culturing the above cells such as RPMI1640 culture medium and MEM culture medium. A serum-supplementing agent such as Fetal Calf Serum (FCS) may be used together.

Predetermined amounts of the immunocyte and the myeloma are mixed well in the above culture medium. PEG solution (e.g., with an average molecular weight of ca.1000-6000) warmed at about 37° C. in advance is added to a final concentration of 30-60% (w/v), and the cells are then mixed to form a desired hybridoma. After sequential addition of an appropriate culture medium, the process of centrifugation and removal of a supernatant is repeated in order to remove the cell fusion-promoting agent which is disadvantageous to the growth of the hybridoma.

The resulting hybridoma is then selected by being cultured in a usual selection medium such as HAT medium containing hypoxanthine, aminopterin and thymidine. The culture in HAT medium is maintained for enough of time (usually from several days to several weeks) so that non-fused cells (cells other than hybridoma) will die. Then, a hybridoma producing a desired antibody is screened and cloned with a limiting dilution method.

In addition to the immunization of the animal other than human with the antigen to obtain the hybridoma, it is possible to obtain a desired humanized antibody having a binding activity to the present protein by sensitizing human lymphocyte with the present protein in vitro and fusing the sensitized lymphocyte with human myeloma having immortality (Japanese Patent Publication Hei.1 (1989)-59878). Alternatively, a transgenic animal having the repertoire of all the genes for human antibody may be administered with the present protein to give a cell producing the present antibody, followed by the fusion of the resulting cell with an immortalized cell to produce the humanized antibody for the present protein PCT WO94/25585, WO93/12227, WO92/03918, WO94/02602).

The hybridoma thus prepared and producing the monoclonal antibody of the present invention may be maintained in passage culture using a usual medium, or may be stored in liquid nitrogen for a long period of time.

The monoclonal antibody may be obtained from the hybridoma by culturing the hybridoma in a usual method and collecting it from its supernatant, or by administering the hybridoma into its compatible mammalian and obtaining it from its ascites. The former method is suitable for the production of a highly purified antibody, and the latter method for a mass production of the antibody.

According to the present invention, a gene encoding an antibody is cloned from the hybridoma, inserted into an appropriate vector, introduced into the host cell and expressed by means of genetic recombination technique to give a recombinant-type monoclonal antibody (for example, Vandamme, A. M. et al., Eur. J. Biochem. (1990) 192, 767-775).

Specifically, mRNA encoding a variable (V) region of the present antibody is isolated from the hybridoma producing the present antibody, by preparing total mRNA with the use of guanidine-ultracentrifugation (Chirgwin, J. M. et al. Biochemstry (1979) 18, 5294-5299), AGPC method (Chomczynski, P. et al., Anal. Biochem. (1987) 162, 156-159) and the like, and preparing a desired mRNA with the use of mRNA Purification Kit (Pharmacia Co.). Alternatively, mRNA may be directly prepared by means of QuickPrep mRNA Purification Kit (Pharmacia Co.).

A cDNA of the variable (v) region of the present antibody is synthesized with the resulting mRNA by means of a reverse trascriptase. For example, the synthesis of cDNA may be done by using AMV Reverse Transcriptase First-strand cDNA Synthesis Kit (Seikagaku Industry Ltd.). Alternatively, the synthesis and amplification of cDNA may be done by using 5'-Ampli FINDER RACE Kit (Clontech Co.) and 5'-RACE method with PCR (Frohman, M. A. et al., Proc. Natl. Acad. Sci., USA (1988) 85, 8998-9002, Belyavsky, A. et al., Nucleic Acids Res. (1989) 17, 2919-2932), etc.

A desired DNA fragment is purified from the resulting PCR products and ligated with a vector DNA. The resulting expression vector is introduced into *E. coli* and the like. A colony containing a desired vector is selected and the vector is prepared from the colony. A nucleotide sequence of the desired DNA is confirmed by a known method such as dideoxy nucleotide chain termination method.

The desired DNA encoding the V region of the present antibody is then integrated into another expression vector containing a DNA encoding the constant region (C region) of a desired antibody.

The gene encoding the present antibody is integrated into an expression vector so that it will be expressed under a control of an expression-regulating region such as an enhancer and promoter. The host cell is then transformed with the expression vector to produce the antibody.

For the expression of the antibody, a DNA encoding a heavy chain (H chain) or a light chain (L chain) may be separately integrated into a different expression vector and used together for co-transformation of the host cell, or a DNA encoding both the H chain and L chain may be integrated into a single expression vector and used for transformation of the host cell (WO 94/11523).

Transgenic animals may be also used for the production of the recombinant-type antibody. For example, the gene for the antibody is inserted within a gene encoding a protein secreted specifically into milk (e.g., goat casein) to give a fused gene. A DNA fragment comprising the fused gene is injected into a goat's embryo, which is then introduced into a female goat. The desired antibody may be obtained from milk of a transgenic goat which will be born by the goat having received the embryo or from milk of off-springs of the transgenic goat. Hormones may be optionally administered to the transgenic goat in order to increase an amount of milk comprising the desired antibody (Ebert, K. M. et al., Bio/Technology (1994) 12, 699-702).

In addition to the above antibodies, various genetic recombinant-type antibodies, which have been artificially modified in order to decrease heteroantigenecity against human, such as a chimera antibody and a humanized antibody may be used in the present invention.

The chimera antibody may be obtained by ligating the above DNA encoding the V region of the antibody with a DNA encoding the C region of a human antibody, integrating the resulting DNA into an expression vector, and introducing the vector into a host cell to produce it. The useful chimera antibody according to the present invention may be prepared according to these conventional methods.

The humanized antibody is also referred to as "reshaped humanized antibody", which is obtained by transplanting the CDR (complementary determining region) of an antibody from mammalian other than human, such as mouse into the CDR of a human antibody. A general technique of genetic recombination for the humanized antibody is also known (European Patent Application EP125023, WO96/02576).

Specifically, a DNA, which is designed so that it can ligate CDR of the mouse antibody with the framework (FR) region of the human antibody, is synthesized with the use of PCR by using as primer a few oligonucleotides having a part overlapping the end regions of both CDR and FR (WO98/13388).

The FR regions linked together through CDRs are selected so that the CDRs will constitute an excellent antigen-binding site. Amino acids in the FR of the V region of the antibody may be substituted, where necessary, so that the CDRs in the reshaped humanized antibody will form an appropriate antigen-binding site (Sato, K. et al., Cancer Res. (1993) 53, 851-856).

The C region in the chimera or humanized antibodies is derived from the human antibody, such as $C_H1$, $C_H2$, $C_H3$, and $C_H4$, for the H chain, and $C\kappa$ and $C\lambda$ for the L chain. The C region of the human antibody may be modified in order to improve stability of the antibody itself or the production thereof.

The chimera antibody consists of the variable region of antibodies derived from mammalian other than human and the constant region of the human antibody. On the other hand, the humanized antibody consists of the CDR of antibodies derived from mammalian other than human, and the FR region and the constant region of the human antibody. The humanized antibody is useful as an effective component in a therapeutic agent according to the present invention since antigenicity of the humanized antibody in human body is lowered.

The antibody used in the present invention may be a fragment of the antibody or a modified fragment thereof, including divalent and monovalent antibodies. For example, the fragment of the antibody includes Fab, F(ab')2, Fv, Fab/c having one Fab and a full Fc, and a single chain Fv (scFv) which is prepared by linking Fv of H chain and Fv of L chain via an appropriate linker. Specifically, an antibody is digested by an enzyme such as papain and pepsin to give the fragment of the antibody. Alternatively, genes encoding the above fragment are constructed and introduced into an expression vector, followed by the expression in a suitable host cell (Co, M. S. et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137).

The scFv is prepared by linking Fv of H chain and Fv of L chain via an appropriate linker, preferably a peptide linker (Huston, J. S. et al., Proc. Natl. Acad. Sci. U.S.A. (1988) 85, 5879-5883). Each Fv of H chain and L chain may be derived from any antibody described in the present specification. The peptide linker used in the linking of V regions includes any single chain peptide having 12-19 amino acids.

A DNA encoding scFV may be prepared with the use of PCR in which amplification is done in the first step by using as template a DNA encoding all or a desired part of the amino acids in H chain or its V region and L chain or its V region and primers defining their both ends, and in the second step by using further a DNA encoding the peptide linker part and a pair of primers designed to ligate each end of the DNA with H chain and L chain, respectively.

Once the DNA encoding scFV is prepared, an expression vector comprising the DNA and a host cell transformed with the vector may be obtained according to a conventional method. The scFV may be produced with the use of the host cell by a conventional method as well.

The DNA encoding the above fragments of the antibody may be obtained, and these fragments of antibody may be expressed by the host cell as well. The "antibody" in the present invention includes these fragments.

As the modified antibody there may be mentioned those coupled with various molecules such as PEG. The antibody may be coupled with a radio isotope, a chemotherapeutic agent, a cytotoxic substance such as a bacteria toxin as well. The "antibody" in the present invention includes also these modified antibodies. These modified antibodies may be prepared by chemically modifying the resulting antibody by a conventional method.

The antibody used in the present invention also includes a bispecific antibody. The bispecific antibody may be the one having antigen-binding sites each of which recognizes a different epitope on the present protein, or the one having antigen-binding sites one of which recognizes an epitope on the present protein, and the other of which recognizes the chemotherapeutic agent or the cytotoxic substance such as a bacteria toxin. In the latter case, it is possible to directly apply the cytotoxic substance to a cell expressing the present protein (cancer cells) so that the cancer cells shall be specifically damaged and inhibited from growing. The bispecific antibody may be prepared by ligating a HL pair of two kinds of antibodies with each other, or by fusing hybridomas producing different monoclonal antibodies to give a hybridoma producing the bispecific antibody. Furthermore, the bispecific antibody may be prepared by genetic engineering technique.

The gene encoding the present antibody may be expressed and obtained by a known method. Where the mammalian cell is used, a conventionally used promoter, a gene for the antibody to be expressed and poly A signal 3'-downstream of the gene are functionally combined to express the gene. As a promoter/enhancer there may be mentioned human cytomegalovirus immediate early promoter/enhancer.

The other promoter/enhancers to be used in the present invention include promoter/enhancers derived from virus such as retrovirus, polyomavirus, adenovirus, and simian virus40 (SV40); and mammalian promoter/enhancer such as human elongation factor 1α (HEF1α).

SV40 promoter/enhancer and HEF1α promoter/enhancer may be used according to Mulligen, Nature (1979) 277, 108 and Mizushima et al., Nucleic Acids Res. (1990) 18, 5322, respectively, in order to easily express the gene.

A replication origin may be derived from SV40, polyoma virus, adenovirus, bovine papilloma virus (BPV), etc. The expression vector may further comprise a selection marker such as aminoglycoside transferase (APH) gene, thymidine kinase (TK) gene, *B. coli* xanthineguanine phosphoribosyl transferase (Ecogpt) gene, and dihydrofolic acid reductase (dhfr) in order to increase the number of copies of the gene in the host cell.

Where the *E. coli* is used, a conventionally used promoter, a signal sequence for secretion and a gene for the antibody to be expressed are functionally combined to express the gene. As a promoter/enhancer there may be mentioned lacz promoter and araB promoter, which are used according to Ward, Nature (1980) 341, 544-546; FASEB J. (1992) 6, 2422-2427, and Better, Science (1988) 240, 1041-1043, respectively.

A pelB signal sequence (Lei, S. P. et al., Bacteriol. (1987) 169, 4379) may be used for the production of the antibody in periplasma of *E. coli*. The antibody produced in the periplasma is separated and appropriately refolded for use.

The present antibody may be produced by any expression system such as eukaryotic and prokaryotic cell expression systems. The eukaryotic cell line includes established cells such as a mammalian cell, an insect cell, filamentous fungus, and yeast. The prokaryotic cell line includes bacteria cells such as *E. coli*. The antibody used in the present invention is preferably expressed in CHO, COS, myeloma, BHK, Vero, and Hela cells.

The transformed host cell is cultured in vitro or in vivo by a known method to produce the desired antibody. The culture medium includes DMEM, MEM, RPMI1640 and IMDM, which may be supplemented with a serum-supplementing agent such as fetal calf serum (FCS).

The thus expressed and produced antibody may be separated from the cell or host animal and purified to homogeneity. The separation and purification of the present antibody may be carried out with the use of an affinity column including Protein A column such as Hyper D, POROS, Sepharose F.F. (Pharmacia Co., etc.). Any other separation and purification methods which are used for usual proteins may be used. For example, the present antibody may be separated and purified with the use of a chromatography column other than the above affinity column, filter, ultra filtration, salting-out and dialysis, and any combination thereof (Antibodies A Laboratory Manual, Ed Harlow, David Lane, Cold Spring Harbor Laboratory, 1988).

Antigen-binding activity (Antibodies A Laboratory Manual, Ed Harlow, David Lane, Cold Spring Harbor Laboratory, 1988) and ligand receptor binding-inhibiting activity (Harada, A. et al., International Immunology (1993) 5, 681-690) may be determined by known methods.

The antigen-binding activity of the present antibody may be determined by ELISA (Enzyme Linked Immuno Sorbent Assay), EIA (Enzyme Immuno Assay), RIA (Radio Immuno Assay) and fluorescence antibody method. In the case of EIA, a sample containing the present antibody such as a culture supernatant of the cell producing the present antibody or a purified antibody is added to a plate coated with the present protein. After addition of a second antibody labeled with an enzyme such as alkaline phosphatase, the plate is incubated and washed. An enzyme substrate such as p-nitrophenyl phosphate is then added to the plate and absorbance is determined in order to evaluate the antigen-binding activity.

The present antibody may also have cytotoxicity activity such as complement-dependent cytotoxicity (CDC) activity and antibody-dependent cell-mediated cytotoxicity (ADCC) activity. The CDC activity in the present specification means cytotoxicity caused by a complement system, and the ADCC activity in the present specification means cytotoxicity caused by a cell having Fcγ receptor (e.g., immunocyte) which binds through its Fcγ receptor to the Fc portion of a specific antibody attached to a target cell.

The presence of CDC or ADCC activity of the present antibody may be determined by a known method (e.g., Current protocols in Immunology, Chapter 7. Immunologic studies in humans, Editor, John E., Coligan et al., John Wiley & Sons, Inc., (1993)).

Specifically, the cytotoxicity activity may be determined as follows:

Preparation of Effecter Cells

Spleen is extracted from CBA/N mouse and the like, and spleen cells are separated in RPMI1640 culture medium (GIBCO Co.). The cells are washed in the same medium containing 10% FBS (Hyclone Co.) and concentration of the cells is adjusted to $5\times10^6$/ml to give an effecter cell preparation.

Preparation of a Complement Solution

A complement solution is prepared by diluting Baby Rabbit Complement (CEDARLANE Co.,) ten times with the above medium containing 10% FBS (Hyclone Co.).

Preparation of Target Cells

The cells expressing the present protein (prostatic adenocarcinoma, ovarian carcinoma, colon adenocarcinoma, etc) are incubated with 0.2 mCi $^{51}$Cr-sodium chromate (Amersham Pharmacia Biotech Co.) in DMEM medium containing 10% FBS for one hour at 37° C. so as to be labeled with a radioisotope. After labeling with the radio isotope, the cells are washed three times with RPMI1640 medium containing 10% FBS and concentration of the cells is adjusted to $2\times10^5$/ml to give a target cell.

Determination of ADCC Activity

The present antibody (50 μl) and the target cell (50 μl) are added into a 96 U-well plate (Beckton Dickinson Co.) and reacted for 15 min. on ice. The effecter cell (100 μl) is then added and the resulting mixture is cultured for 4 hours in $CO_2$ incubator. The final concentration of the antibody is adjusted to 0 or 10 μg/ml. After the completion of the culture, 100 μl of supernatant is recovered and subjected to the determination of radioactivity by means of a gamma counter (COBRAIIAUTO-GMMA, MODEL D5005, Packard Instrument Company). The cytotoxicity (%) is calculated based on the formula: $(A-C)/(B-C)\times100$ wherein "A" is the radio activity (cpm) of each test sample, "B" is the radio activity (cpm) of a sample mixed with 1% NP-40 (Nakarai Ltd.), and "C" is the radio activity (cpm) of a sample containing only the target cell.

Determination of CDC Activity

The present antibody (50 μl) and the target cell (50 μl) are added into a 96 U-well plate (Beckton Dickinson Co.) and reacted for 15 min. on ice. The complement solution (100 μl) is then added and the resulting mixture is cultured for 4 hours in $CO_2$ incubator. The final concentration of the antibody is adjusted to 0 or 3 μg/ml. After the completion of the culture, 100 μl of supernatant is recovered and subjected to the determination of radioactivity by means of the gamma counter. The cytotoxicity is determined by the same way as in ADCC activity.

[Anti-Cancer Agent According to the Present Invention]

An effective amount of administration of the anti-cancer agent of the present invention usually ranges from 0.001 mg~1,000 mg per 1 kg weight, or 0.01~100,000 mg/body of patient, being, however, not limited to these ranges. The present agent may be administered before or after the occurrence of clinical symptom. The present agent may be prepared according to a known method (Remington's Pharmaceutical Science, latest edition, Mark Publishing Company, Easton USA), while being optionally mixed together with pharmaceutically acceptable carriers or additives. These pharmaceutically acceptable carriers or additives include, for example, water, pharmaceutically acceptable organic solvent, collagen, polyvinylalcohol, polyvinylpyrrolidone, carboxylvinylpolymer, sodium carboxylmethylcellulose, sodium polyacrylate, sodium alginate, aqueous dextran, sodium carboxylmethylstarch, pectin, methylcellulose, ethylcellulose, xanthan gum, arabic gum, casein, agarose, polyethylenglycol, diglycerine, glycerine, propylene glycol, petroleum jelly, paraffin, stearic alcohol, stearic acid, human serum albumin (HSA), mannitol, sorbitol, lactose, and pharmaceutically acceptable surfactant. The carries or additives may be optionally selected from the above-listed substances depending on a formulation type of the present agent. A preparation for injection may be a solution in solvent such as physiological saline, buffer solution and glucose solution supplemented with absorption-inhibiting agent such as Tween80, Tween20, gelatin, and HSA. A preparation of the present agent may be lyophilized and dissolved before use, including sugars or sugar alcohols such as mannitol and glucose as an excipient for lyophilization. The present agent is usually administered parentally, for example, by injection (subcutaneously, intravenouly, intramuscularly, intraperitoneally, etc.), percutaneously, permucously, administration through nose or lung, but may be administered orally as well.

[Method of Screening a Substance which Binds to the Above Protein or a Partial Peptide Thereof]

The present protein is useful in screening of a substance which binds to it. Thus, it is used in a method of screening a substance which binds to the present protein, which comprises bringing a sample seemingly containing the substance in contact with said protein, detecting a binding activity between the sample and said protein and selecting a substance which has the binding activity.

The present protein used in the screening method may be a recombinant one, naturally occurring one, or a partial peptide thereof. Any material may be used as a sample of the method, including, for example, cell extracts, cell culture supernatants, products by fermenting bacteria, extracts from marine organisms, plant extracts, (crudely) purified proteins, peptides, non-peptide compounds, synthetic low molecular compounds, and natural compounds. The present protein to be brought in contact with the sample may be used as a purified one, a solubilized one, a complex with a carrier, a fused one with other proteins, an expressed one on a cell membrane, or a membrane component.

For example, a protein such as a ligand binding to the present protein may be screened with the use of any method known for those skilled in the art. These methods include Immunoprecipitation (Harlow, E. and Lane, D.: Antibodies, pp. 511-552, Cold Spring Harbor Laboratory publications, New York (1988)), West-Western blotting (Skolnik, E. Y. et al., Cell (1991) 65, 83-90), Two-hybrid system using cells (Fields, S., and Sternglantz, R., Trend. Genet. (1994) 10, 286-292, Dalton S, and Treisman R., (1992) Characterization of SAP-1, a protein recruited by serum response factor to the c-fos serum response element, Cell, 68, 597-612, [MATCHMAKER Two-Hybrid System][Mammalian MATCHMAKER Two-Hybrid Assay Kit][MATCHMAKER One-Hybrid System] (Clontech Co.), [HybriZAP Two-Hybrid Vector System] (Stratagene Co.), Affinity chromatography, and biosensor using surface plasmon resonance phenomenon.

The method for the separation of the compounds including protein, which bind to the present protein, includes known methods such as a screening method wherein the fixed present protein is reacted with a synthesized compound, a bank of natural materials, and a random phage display library, and a molecular which can bind to the present protein is selected;

and a screening method wherein a high through-put reaction is done by means of combinatorial chemistry technique (Wrighton N C; Farrell F X; Chang R; Kashyap A K; Barbone F P; Mulcahy L S; Johnson D L; Barrett R W; Jolliffe L K; Dower W J; Small peptides as potent mimetics of the protein hormone erythropoietin, Science (UNITED STATES) Jul. 26, 1996, 273 p 458-464, Verdine G L., The combinatorial chemistry of nature, Nature (ENGLAND) Nov. 7, 1996, 384 p 11-13, Hogan J C Jr., Directed combinatorial chemistry, Nature (ENGLAND) Nov. 7, 1996, 384 p 17-17).

Since the compound which can be separated by the screening method according to the present invention may be a substance which inhibits the binding between the present protein and ligand, it will be utilized in an anti-cancer agent. Thus, the anti-cancer agent may be prepared by combining the compound separated by the present screening method with pharmaceutically acceptable carries.

[Others]

An antisense oligonucleotide (DNA) having a nucleotide sequence substantially complementary to a DNA encoding the present protein or a partial polypeptide thereof includes any antisense DNA as long as it has a nucleotide sequence substantially complementary to said DNA and has a function to inhibit the expression of the same DNA. The "nucleotide sequence substantially complementary" means, for example, that it has homology preferably of about 90% or more, more preferably of about 95% or more, most preferably of 100% to the whole or partial sequence of a nucleotide sequence complementary to the present DNA. Any nucleic acid sequence (a modified DNA or RNA) which shows a function similar to that of the antisense DNA is also included in the antisense DNA according to the present invention. These antisense DNAs may be prepared with a known DNA synthesizer.

The present DNA or gene comprising thereof may be used as a probe to detect abnormality in the DNA or its mRNA (genetic abnormality) encoding the present polypeptide or its partial peptide. They are therefore useful as a genetic diagnosis agent for detecting damage, mutation and under-expression of the DNA or mRNA; or for detecting increase and over-expression of the DNA or mRNA. The genetic diagnosis with use of the present DNA may be done by a known method such as Northern hybridization and PCR-SSCP (Genomics vol. 5, 874-879 (1989), Proceedings of the National Academy of Science of the United States of America, vol. 86, 2766-2770 (1989)).

The function of the protein according to the present invention can be effected in a patient in whom the present DNA or gene dose not normally function due to its abnormality, deletion or under-expression by a known method such as (1) the one in which the present DNA or gene is introduced into the patient and expressed by gene therapy with the use of an appropriate vector such as retrovirus vector, adenovirus vector and adenovirus-associated virus vector; and (2) the one in which they are injected into the patient.

The present DNA or gene may be also administered alone or in combination with an auxiliary to promote uptake by means of a gene gun or a catheter such as a hydrocatheter.

Single mutation in the present DNA or gene (cSNP), which is different from each individual, may be found by doing PCR of a chromosomal DNA extracted from human blood or tissue with the use of a synthetic DNA primer prepared based on the whole or partial nucleotide sequence of the present DNA or gene, and determining the nucleotide sequence of the PCR products. Individual constitution may be predicted by such cSNP, making possible to develop a drug suitable for each person.

Causal or responsible genes for human disorders may be searched and detected by isolating an orthologue (homologue or counterpart)) gene corresponding to the present DNA or gene in a model animal such as mouse, and making a model animal of the disorders with the use of knock out technique.

The abbreviation for a base and amino acid is shown in the present specification in accordance with IUPAC-IUB Commission on Biochemical Nomenclature or conventional methods, and an optical isomer of the amino acid, if any, means its L-isomer unless otherwise instructed.

EXAMPLES

The present invention will by further explained by the following examples, which do not limit the scope of the present invention. The genetic procedures in the examples are done in accordance with those described in Current protocols in molecular biology (edited by Frederick M. Ausubel et al., 1987).

(1) Construction of cDNA Library Derived from Human Adult Whole Brain, Human Amygdala, Human Adult Hippocampus, and Human Fetal Whole Brain A double-stranded cDNA was synthesized by SuperScriptII reverse transcriptase kit (Invitrogen Co.) with the use of an oligonucleotide having NotI site (GACTAGTTCTAGATCGCGAGCGGCCGCCC(T)15)(SEO ID NO: 3) (Invitrogen Co.) as a primer, and mRNA derived from human adult whole brain, human amygdala, human adult hippocampus, and human fetal whole brain (Clontech Co.) as a template. An adapter having SalI site (Invitrogen Co.) was ligated with the resulting cDNAs. After digestion with NotI, the cDNAs were subjected to electrophoresis on a low-melting agarose of 1% to purifiy cDNA fragments with 3 kb or more.

The thus purified cDNA fragments were ligated with pBluescript II SK+ plasmid treated with SalI-NotI restriction enzymes. The resulting recombinant plasmids were introduced into *E. coli* DH10B strain (Invitrogen Co.) by an electroporation method.

(2) Screening (No.1)

Clones were randomly picked up from the thus constructed cDNA library and spotted on a membrane. A mixture of oligoDNAs (21 base-long each) prepared on the basis of the nucleotide sequences of about 1,300 clones which had been analyzed about their whole nucleotide sequences were labeled with DIG by terminal transferase at their 3'-ends. Overlapping clones which will appear repeatedly were then removed by dot hybridization with use of the mixture of the above labeled oligoDNAs as a probe (Current protocols in molecular biology (edited by Frederick M. Ausubel et al., 1987).

After the transcription and translation system in vitro (Promega Co., TNT T7 Quick Coupled Transcription/Translation System cat.no.L1107), clones expressing products with 50 kDa or more were selected.

The terminal nucleotide sequences of the selected clones were determined, and the homology search was done on nr database (all GenBank+EMBL+DDBJ+PDB sequences, but no EST, STS, GSS or phase 0.1 or 2 HTGS seqeunces) with the use of the resulting sequences as a query in accordance with homology search program BLASTN2.2.1 (Altshul, Stephen F., Thomas L. Madden, Alejandro A., Schaffer, Jinghui Zhang, Zheng Zhang, Webb Miller, and David J. Lipman (1997), "Gapped BLAST and PSI-BLAST: a new generation of protein search programs.", Nucleic acids Res. 25:3389-3402). As a result, a gene having no homologous gene, i.e., a novel gene, is subjected to the whole nucleotide sequence analysis.

Screening (No.2)

The terminal sequences of 3'- and 5'-ends of the above cDNAs were aligned with human genomic sequence (ncbi.nlm.nih. gov/genomes/H sapiens/) with the use of homology search program BLASTN2.2.1.

Genes were picked up from a genome region inserted between them by the use of Genscan program (computer software for predicting a gene from genome sequences) (Burge, C. and Karlin, S. 1987, Prediction of complete gene structures in human genomic DNA, J. Mol. Biol., 268, 78-94). Homology search was done on merged, which had been prepared by combining human cDNA sequences determined by KAZUSA DNA Institute and *Homo sapiens* database of GenBank (except EST and genome) without overlapping data, with the use of the selected genes as a query in accordance with homology search program BLASTN2.1.3. When a novel long-ORF gene (with 1,200 bp or more of cds according to the prediction by Genscan) was found, the full-length sequences of its 5'- and 3'-ends were determined.

Determination of the nucleotide sequence was carried out by means of a DNA sequencer (ABI PRISM377) and a reaction kit manufactured by PE Applied Bio System Co. Most of the sequences were determined by a diterminator method on shotgun clones, and parts of them were determined by a primer-walking method with the use of oligonucleotides that were synthesized based on the thus determined nucleotide sequences.

The novel DNAs or genes were screened in the above ways. As a result, a clone pj01304 was found. Furthermore, the 3'- and 5'-end sequences of about 100,000 clones isolated from brain cDNA library prepared by Ohara et al. and about 2,000 full-length clones were assembled together, and grouping of cDNA clones derived from the same gene was done.

As a result, a clone hj05443 comprising an upstream region of the clone pj01304 was finally found in a group containing the clone pj01304.

The upstream region of the clone pj01304 was then excised from the clone hj05443 and ligated with the clone pj01304 to give a clone pj01304s1 (KIAA1742) comprising the novel DNA or gene represented in SEQ ID NO.1 or NO.2 according to the present invention. The nucleotide sequence from 1 bp to 820 bp of the clone pj01304s1 is derived from the clone hj05443, and that from 821 bp to 5,035 bp is derived from the clone pj01304.

(3) Expression of the Protein Encoded by the Present Gene

A gene product was expressed from the cDNA clone pj01304 with the use of the transcription and translation system in vitro (Promega Co., TNT T7 Quick Coupled Transcription/Translation System cat.no.L1107).

The product incorporated with $^{35}$S-labeled methionine was subjected to SDS-PAGE (12.5%). After drying of a gel, autoradiography was done with the use of BAS2000 (Fuji film) system to detect the gene product of the clone pj01304. As a result, a band, which was presumed to be a transcription/translation product of the clone pj01304, was observed at a point corresponding to a marker with 135 kDa.

As a molecular weight of the protein encoded by the pj01304 consisting of 1,137 amino acids from a first methionine is presumed to be about 124 kDa, the presumed molecular weight was coincided well with the above result.

(4) Homology Research of the Present DNA

The homology search of the whole nucleotide sequence thus determined was done on the known nr data in accordance with homology search program BLASTN2.2.1 (Altshul, Stephen F., Thomas L. Madden, Alejandro A., Schaffer, Jinghui Zhang, Zheng Zhang, Webb Miller, and David J. Lipman (1997), "Gapped BLAST and PSI-BLAST: a new generation of protein search programs.", Nucleic acids Res. 25:3389-3402). As a result, the present DNA has homology to a gene shown in Table 1. Table 1 shows information about the gene (homologous gene) such as its name, data base ID, species, length of protein, etc. The meaning of each item in Table 1 is as follows:

"Homologous region, clone": the starting and ending points of the homologous region in the present clone;

"Homologous region, homologous gene": the starting and ending points of the homologous region in the homologous gene;

"Score": the higher this value is, the higher credibility is;

"E-value": the closer this value comes to "0", the higher credibility become;

"Homology": the percentage of identical amino acids in the homologous region; and "Percentage of the homology region": the percentage of the homologous region in the homologous gene.

TABLE 1

| Homologous region | | | | Homology Value | | | |
|---|---|---|---|---|---|---|---|
| Clone | | Homologous gene | | | | | Percentage of the homology |
| from | to | from | to | Score | E-value | Homology | region |
| 59 | 913 | 236 | 1125 | 423 | e-117 | 31% (287/923) | 73% |

| Homologous gene | | | | |
|---|---|---|---|---|
| Name | Data base | Species | Length of protein | Publication |
| CG2019 | gbIAAF51938.11 | Dm | 1218 | — |

(5) Search of Domains

The DNA according to the present invention (KIAA1742) is a gene with 5,035 bp encoding a protein with 1,245 amino acids. Motif search by the use of HMMER2.1.1 (S. R. Eddy. Profile hidden Markov models. Bioinfomatics 14:755-763, 1998) revealed the existence of a motif of Patched family which is involved in a signal of hedgehog-smoothend in the region of amino acids No. 145-954.

Further, the search with the use of Sosui (Bioinformatics (1998) May; 14(4):378-379) predicted the presence of 12 transmembrane regions as shown in Table2. It was assumed that the region of amino acids No.39-328 (a region between the first and second transmembrane regions) and the region of amino acids No.560-802 (a region between the seventh and eighth transmembrane regions) constituted a large loop, which was very similar to the structure of Patched (Cell 59, 751 (1989); Cancer Letter (2001) 173, 1-7) as shown in FIG. 1.

TABLE 2

| SEQ ID NO | No. | N terminal | transmembrane region | C terminal | length |
|---|---|---|---|---|---|
| 6 | 1 | 14 | VAVLMLCLAVIFLCTLAGLLGARLP | 38 | 25 |
| 7 | 2 | 329 | LVQDTVYPLLALVAIFFGMALYLRS | 353 | 25 |
| 8 | 3 | 357 | TLMVLLGVLGSLLVAFFLYQVAFRM | 381 | 25 |
| 9 | 4 | 385 | PFVNLAALLLLSSVCANHTLIFFDL | 409 | 25 |
| 10 | 5 | 433 | FGYLLLVSGLTTSAAFYASYLSRLP | 457 | 25 |
| 11 | 6 | 463 | ALFMGTAVLVHLALTLVWLPASAVL | 487 | 25 |
| 12 | 7 | 535 | FQRLLPCGVIKFRYIWICWFAALAA | 559 | 25 |
| 13 | 8 | 803 | SLSTEPAVVLGLALALAFATLLLGT | 827 | 25 |
| 14 | 9 | 831 | PLSLFSVAAVAGTVLLTVGLLVLLE | 855 | 25 |
| 15 | 10 | 864 | LFLSASVGLSVDFTVNYCISYHLCP | 888 | 25 |
| 16 | 11 | 902 | QTSCATAVGAAALFAAGVLMLPATV | 926 | 25 |
| 17 | 12 | 934 | IILMMVKCVSCGFASFFFQSLCCFF | 958 | 25 |

Brief Explanation of Table 2

The amino acid sequences and locations of the predicted 12 transmembrane regions are shown in Table 2. "N terminal" and "C-terminal" show the number of the amino acid at N-terminal and C-terminal, respectively. "Length" means the length of transmembrane region.

"Patched" was found in *Drosophila* as a protein having 12 transmembrane regions, which functions as a tumor suppressor of blocking a signal of Smoothend. Patched has two large hydrophilic and extracellular loops, and transmits the signal through direct or indirect interaction with Smoothend. However, it is assumed that the binding of Hedgehog will release the blocking of the signal of Smoothend and cause basal cell carcinoma. Patched is known to control the transcription of members of TGFβ such as BMP or Wnt families (EMBO J (1998) 17, 3505-3511), Cancer Letter (2001) 173, 1-7). It has been reported that Hptc (Human gene homologue to ptc) is involved in skin carcinoma (Am J Pathol (2001) 158, 381-385, PNAS (1999) 96, 5117-5122).

The present protein belonging to Patched family has homology of 31% to Dispatched of the same family, and it is the protein having 12 transmembrane regions like Patched. Gene expression profiling showed that increase of the expression of the present gene was observed in prostatic adenocarcinoma and ovarian carcinoma in, it is assumed that the present gene acts as an oncogene, but not as a tumor suppressor gene like Patched. It is conceived that the present protein will interact with Smoothend or other proteins through the two large extracellular loops and transmit cancer signal. Or it may competitively act against the binding between Hedgehog and Patched, and transmit cancer signal.

In view of the above knowledge and information about the biological activity (function) of the present DNA, it is considered that the present DNA is a cancer-associated gene, and that it is possible to inhibit cancer by blocking the binding of the present protein to its ligand.

Accordingly, the present antibody is used not only in the detection of the present protein, but also as an agent for the treatment or prevention of cancers such as prostatic adenocarcinoma and ovarian carcinoma (6) Real-Time PCR Analysis of the Transcription Products An amount of the transcription product of the present gene were analyzed by using cDNA in each tissue with ABI PRISM® 7700 Sequence Detection System (ABI Co.). The expression amount of GAPDH gene was analyzed with Pre-Developed TaqMan PCR Assay Kit (ABI Co. #4310884E). Master Mix was prepared by mixing 1.25 μl of 20× Control Mix (GAPDH), 6.25 μl of DEPC-treated water (Ambion Co. #9920) and 12.5 μl of TaqMan Universal PCR Master Mix (ABI Co. #430-4437). After the addition of 5 μl of MTC Panel cDNA (Clontech Co.) to the Master Mix to a final volume of 25 μl, gene amplification was done by 2 min. at 50° C., 10 min. at 95° C., and repeating 40 cycles of 15 sec. at 95° C. and 1 min. at 60° C. on MicroAmp Optical 96-wel Reaction Plate (ABI Co. #N801-0560). Human MTC™ Panel I (K1420-1), Human MTC™ Panel II (K1421-1) and Tumor MTC™ Panel I (K1422-1) were used as MTC Panel cDNA.

An expression amount of the present gene was analyzed by amplification with the use of a primer 1742-3538 (5'-CAGCACTCACACGTCAGGCT-3') (SEQ ID NO: 4), and a primer 1742-3658 (5'-AGAAATACCTTCGGGCTCCAG-3')(SEQ ID NO: 5). 0.5 μl of the primer 1742-3538 (10 μM), 0.5 μl of the primer 1742-3658 (10 μM), 6.5 μl of DEPC-treated water, 12.5 μl of SYBR Green PCR Master Mix (ABI Co. #4309155) were mixed together to a final volume of 20 μl, followed by the addition of 1 μl of MTC Panel cDNA (Clontech Co.) and 4 μl of DEPC-treated water to a final volume of 25 μl. Gene amplification was done by 2 min. at 50° C., 10 min. at 95° C., and repeating 40 cycles of 20 sec. at 95° C., 30 sec. at 59° C., and 30 sec. at 72° C. on MicroAmp Optical 96-wel Reaction Plate (ABI Co. #N801-0560) with the use of ABI PRISM® 7700 Sequence Detection System (ABI Co.). Relative values were calculated based on a standard curve of control cDNA attached to MTC Panel with the use of the expression amount of GAPDHgene as a standard control. A vector comprising the present gene cloned in pBluescript (40 pg/μl) was serially diluted 5 times and the resulting solutions were then used as reference. The relative values in each tissue obtained by dividing the expression amount of the present gene by that of GAPDH gene are summarized and compared among one another in Table 3.

In Table 3, figures in the right column indicate the expression amount of the KIAA1742 gene, which was normalized with the expression amount of GAPDH gene in each tissue, and shown as a relative value against prostate of value "1".

Table 3 clearly shows that the high values are obtained in prostatic adenocarcinoma and ovarian carcinoma.

TABLE 3

| Tissue | KIAA1742/GAPDH |
|---|---|
| Heart | 0.28 |
| Brain | 36.60 |
| Placenta | 1.91 |
| Lung | 1.78 |
| Liver | 3.85 |
| skeletal muscle | 0.06 |
| Kidney | 0.57 |
| Pancreas | 3.60 |
| Spleen | 2.57 |
| Thymus | 0.48 |
| Prostate | 1.00 |
| Testis | 5.87 |
| Ovary | 1.10 |
| small intestine | 6.81 |
| Colon | 13.03 |
| peripheral blood leukocyte | 0.27 |
| breast carcinoma GI-101 | 0.61 |
| lung carcinoma LX-1 | 0.46 |
| colon adenocarcinoma CX-1 | 8.87 |
| lung carcinoma GI-117 | 0.12 |
| prostatic adenocarcinon PC3 | 229.78 |
| colon adenocarcinoma GI-112 | 0.99 |
| ovarian carcinoma | 28.36 |
| pancreatic adenocarcinoma GI-103 | 0.87 |

(7) Location on Chromosome

It was further confirmed that the present gene was expressed in cerebellum with the use of PT-PCR Coupled ELISA Alignment of the DNA sequence of the present clone with a human genomic library (ncbi.nlm.nih.gov/genomes/H_sapiens/) showed that the present gene was located on chromosome 15.

(8) Preparation of pj01304s1 (KIAA1742) Gene Family

Homology search of the DNA sequence of the pj01034s1 gene was done on human genomic sequences (ncbi.nlm.nih.gov/genomes/H sapiens/) in accordance with BLSTN2.2.1 hit a particular genomic fragment (GenBank ID NT_010194.6).

The pj01304GS gene, which has a high homology to the pj01304s1 gene (100% at DNA level and 100% at protein level; aligned by GenWorks (Intelligenetics Co.)), was then found with the use of Genscan program (Burge, C. and Karlin, S. 1987, Prediction of complete gene structures in human genomic DNA, J. Mol. Biol., 268, 78-94: computer software for predicting a gene from genome sequences). The pj01304GS gene has 4,479 bp, which encodes a protein having 1,492 amino acids. Its nucleotide sequence and amino acid sequence are shown as SEQ ID NO.2.

The alignment (SEQ ID NO: 20) between the pj01304GS gene (SEQ ID NO: 19) and the pj01304s1 gene (SEQ ID NO: 18) is shown in Table 4. As seen from Table 4, an amino acid sequence of No. 248-1,492 encoded by the pj01304GS gene is identical with an amino acid sequence of No. 1-1,245 encoded by the pj01304s1 gene, showing that the pj01304GS gene has a nucleotide sequence encoding an amino acid sequence of No.1-247 located 5' upstream of the pj01304s1 gene. Accordingly, it is considered that both the genes are generated from the same genome by an alternative splicing. It is also considered that as the pj01304GS gene has the same domains as the pj01304s1 gene, it will show similar activities. Thus, the pj01304GS gene and protein encoded thereby are included in the DNA and protein according to the present invention, respectively.

Those skilled in the art may easily prepare those genes by, for example, RT-PCR. Thus, PCR is done by the use of an upstream primer (5'-ATGGGAAGAAAGACCCAACC-3':1-20 by of the SEQ ID NO.2) and a downstream primer (SEQ ID NO: 21)(5'-CAAGTCCTGGCAGGGAACTG-3': reverse complement sequence of 588-607 by of the SEQ ID NO:2), and cDNA as a template obtained by reverse transcription from human adult cerebellum mRNA with random primers. The resulting DNA is then ligated with the pj01304s1 gene by known methods such as Chuan Li et al., Ligation independent cloning irrespective of restriction site compatibility, Nucleic Acids Res. 1997 25:20 (4165-4166) to give a clone encoding the pj01304GS protein.

TABLE 4

```
pj01304GS   MGRKTQPDAS PHWGGEEGAE RAGNLAGLKP PASTRGVQRG EVRAWSSPSI    50
pj01304s1   ---------- ---------- ---------- ---------- ----------
Consensus   .......... .......... .......... .......... ..........    50

pj01304GS   RLEGAYACAR APRRRCRRHR RRRRRRRGFS TSARTAVPPT GMDGDSSSSS   100
pj01304s1   ---------- ---------- ---------- ---------- ----------
Consensus   .......... .......... .......... .......... ..........   100

pj01304GS   GGSGPAPGPG PEGEQRPEGE PLAPDGGSPD STQTKAVPPE ASPERSCSLH   150
pj01304s1   ---------- ---------- ---------- ---------- ----------
Consensus   .......... .......... .......... .......... ..........   150

pj01304GS   SCPLEDPSSS SGPPPTTSTL QPVGPSSPLA PAHFTYPRAL QEYQGGSSLP   200
pj01304s1   ---------- ---------- ---------- ---------- ----------
Consensus   .......... .......... .......... .......... ..........   200

pj01304GS   GLGDRAALCS HGSSLSPSPA PSQRDGTWKP PAVQHHVVSV RQERAFQMPK   250
pj01304s1   ---------- ---------- ---------- ---------- -------MPK     3
Consensus   .......... .......... .......... .......... .......MPK   250

pj01304GS   SYSQLIAEWP VAVLMLCLAV IFLCTLAGLL GARLPDFSKP LLGFEPRDTD   300
pj01304s1   SYSQLIAEWP VAVLMLCLAV IFLCTLAGLL GARLPDFSKP LLGFEPRDTD    53
Consensus   SYSQLIAEWP VAVLMLCLAV IFLCTLAGLL GARLPDFSKP LLGFEPRDTD   300
```

TABLE 4-continued

| | | |
|---|---|---|
| pj01304GS | IGSKLVVWRA LQALTGPRKL LFLSPDLELN SSSSHNTLRP APRGSAQESA | 350 |
| pj01304s1 | IGSKLVVWRA LQALTGPRKL LFLSPDLELN SSSSHNTLRP APRGSAQESA | 103 |
| Consensus | IGSKLVVWRA LQALTGPRKL LFLSPDLELN SSSSHNTLRP APRGSAQESA | 350 |
| pj01304GS | VRPRRMVEPL EDRRQENFFC GPPEKSYAKL VFMSTSSGSL WNLHAIHSMC | 400 |
| pj01304s1 | VRPRRMVEPL EDRRQENFFC GPPEKSYAKL VFMSTSSGSL WNLHAIHSMC | 153 |
| Consensus | VRPRRMVEPL EDRRQENFFC GPPEKSYAKL VFMSTSSGSL WNLHAIHSMC | 400 |
| pj01304GS | RMEQDQIRSH TSFGALCQRT AANQCCPSWS LGNYLAVLSN RSSCLDTTQA | 450 |
| pj01304s1 | RMEQDQIRSH TSFGALCQRT AANQCCPSWS LGNYLAVLSN RSSCLDTTQA | 203 |
| Consensus | RMEQDQIRSH TSFGALCQRT AANQCCPSWS LGNYLAVLSN RSSCLDTTQA | 450 |
| pj01304GS | DAARTLALLR TCALYYHSGA LVPSCLGPGQ NKSPRCAQVP TKCSQSSAIY | 500 |
| pj01304s1 | DAARTLALLR TCALYYHSGA LVPSCLGPGQ NKSPRCAQVP TKCSQSSAIY | 253 |
| Consensus | DAARTLALLR TCALYYHSGA LVPSCLGPGQ NKSPRCAQVP TKCSQSSAIY | 500 |
| pj01304GS | QLLHFLLDRD FLSPQTTDYQ VPSLKYSLLF LPTPKGASLM DIYLDRLATP | 550 |
| pj01304s1 | QLLHFLLDRD FLSPQTTDYQ VPSLKYSLLF LPTPKGASLM DIYLDRLATP | 303 |
| Consensus | QLLHFLLDRD FLSPQTTDYQ VPSLKYSLLF LPTPKGASLM DIYLDRLATP | 550 |
| pj01304GS | WGLADNYTSV TGMDLGLKQE LLRHFLVQDT VYPLLALVAI FFGMALYLRS | 600 |
| pj01304s1 | WGLADNYTSV TGMDLGLKQE LLRHFLVQDT VYPLLALVAI FFGMALYLRS | 353 |
| Consensus | WGLADNYTSV TGMDLGLKQE LLRHFLVQDT VYPLLALVAI FFGMALYLRS | 600 |
| pj01304GS | LFLTLMVLLG VLGSLLVAFF LYQVAFRMAY FPFVNLAALL LLSSVCANHT | 650 |
| pj01304s1 | LFLTLMVLLG VLGSLLVAFF LYQVAFRMAY FPFVNLAALL LLSSVCANHT | 403 |
| Consensus | LFLTLMVLLG VLGSLLVAFF LYQVAFRMAY FPFVNLAALL LLSSVCANHT | 650 |
| pj01304GS | LIFFDLWRLS KSQLPSGGLA QRVGRTMHHF GYLLLVSGLT TSAAFYASYL | 700 |
| pj01304s1 | LIFFDLWRLS KSQLPSGGLA QRVGRTMHHF GYLLLVSGLT TSAAFYASYL | 453 |
| Consensus | LIFFDLWRLS KSQLPSGGLA QRVGRTMHHF GYLLLVSGLT TSAAFYASYL | 700 |
| pj01304GS | SRLPAVRCLA LFMGTAVLVH LALTLVWLPA SAVLHERYLA RGCARRARGR | 750 |
| pj01304s1 | SRLPAVRCLA LFMGTAVLVH LALTLVWLPA SAVLHERYLA RGCARRARGR | 503 |
| Consensus | SRLPAVRCLA LFMGTAVLVH LALTLVWLPA SAVLHERYLA RGCARRARGR | 750 |
| pj01304GS | WEGSAPRRLL LALHRRLRGL RRAAAGTSRL LFQRLLPCGV IKFRYIWICW | 800 |
| pj01304s1 | WEGSAPRRLL LALHRRLRGL RRAAAGTSRL LFQRLLPCGV IKFRYIWICW | 553 |
| Consensus | WEGSAPRRLL LALHRRLRGL RRAAAGTSRL LFQRLLPCGV IKFRYIWICW | 800 |
| pj01304GS | FAALAAGGAY IAGVSPRLRL PTLPPPGGQV FRPSHPFERF DAEYRQLFLF | 850 |
| pj01304s1 | FAALAAGGAY IAGVSPRLRL PTLPPPGGQV FRPSHPFERF DAEYRQLFLF | 603 |
| Consensus | FAALAAGGAY IAGVSPRLRL PTLPPPGGQV FRPSHPFERF DAEYRQLFLF | 850 |
| pj01304GS | EQLPQGEGGH MPVVLVWGVL PVDTGDPLDP RSNSSLVRDQ AFSASGPEAQ | 900 |
| pj01304s1 | EQLPQGEGGH MPVVLVWGVL PVDTGDPLDP RSNSSLVRDQ AFSASGPEAQ | 653 |
| Consensus | EQLPQGEGGH MPVVLVWGVL PVDTGDPLDP RSNSSLVRDQ AFSASGPEAQ | 900 |
| pj01304GS | RWLLALCGRA RNQSFFDTLQ EGWPTLCFVE TLQRWMESPS CARLGPDLCC | 950 |
| pj01304s1 | RWLLALCGRA RNQSFFDTLQ EGWPTLCFVE TLQRWMESPS CARLGPDLCC | 703 |
| Consensus | RWLLALCGRA RNQSFFDTLQ EGWPTLCFVE TLQRWMESPS CARLGPDLCC | 950 |
| pj01304GS | GHSDFPWAPQ FFLHCLKMMA LEQGPDGTQD LGLRFDAHGS LAALVLQFQT | 1000 |
| pj01304s1 | GHSDFPWAPQ FFLHCLKMMA LEQGPDGTQD LGLRFDAHGS LAALVLQFQT | 753 |
| Consensus | GHSDFPWAPQ FFLHCLKMMA LEQGPDGTQD LGLRFDAHGS LAALVLQFQT | 1000 |
| pj01304GS | NFRNSPDYNQ TQLFYNEVSH WLAAELGMAP PGLRRGWFTS RLELYSLQHS | 1050 |
| pj01304s1 | NFRNSPDYNQ TQLFYNEVSH WLAAELGMAP PGLRRGWFTS RLELYSLQHS | 803 |
| Consensus | NFRNSPDYNQ TQLFYNEVSH WLAAELGMAP PGLRRGWFTS RLELYSLQHS | 1050 |
| pj01304GS | LSTEPAVVLG LALALAFATL LLGTWNVPLS LFSVAAVAGT VLLTVGLLVL | 1100 |
| pj01304s1 | LSTEPAVVLG LALALAFATL LLGTWNVPLS LFSVAAVAGT VLLTVGLLVL | 853 |
| Consensus | LSTEPAVVLG LALALAFATL LLGTWNVPLS LFSVAAVAGT VLLTVGLLVL | 1100 |

TABLE 4-continued

```
pj01304GS   LEWQLNTAEA LFLSASVGLS VDFTVNYCIS YHLCPHPDRL SRVAFSLRQT   1150
pj01304s1   LEWQLNTAEA LFLSASVGLS VDFTVNYCIS YHLCPHPDRL SRVAFSLRQT    903
Consensus   LEWQLNTAEA LFLSASVGLS VDFTVNYCIS YHLCPHPDRL SRVAFSLRQT   1150

pj01304GS   SCATAVGAAA LFAAGVLMLP ATVLLYRKLG IILMMVKCVS CGFASFFFQS   1200
pj01304s1   SCATAVGAAA LFAAGVLMLP ATVLLYRKLG IILMMVKCVS CGFASFFFQS    953
Consensus   SCATAVGAAA LFAAGVLMLP ATVLLYRKLG IILMMVKCVS CGFASFFFQS   1200

pj01304GS   LCCFFGPEKN CGQILWPCAH LPWDAGTGDP GGEKAGRPRP GSVGGMPGSC   1250
pj01304s1   LCCFFGPEKN CGQILWPCAH LPWDAGTGDP GGEKAGRPRP GSVGGMPGSC   1003
Consensus   LCCFFGPEKN CGQILWPCAH LPWDAGTGDP GGEKAGRPRP GSVGGMPGSC   1250

pj01304GS   SEQYELQPLA RRRSPSFDTS TATSKLSHRP SVLSEDLQLH DGPCCSRPPP   1300
pj01304s1   SEQYELQPLA RRRSPSFDTS TATSKLSHRP SVLSEDLQLH DGPCCSRPPP   1053
Consensus   SEQYELQPLA RRRSPSFDTS TATSKLSHRP SVLSEDLQLH DGPCCSRPPP   1300

pj01304GS   AFASPRELLL DHQAVFSQCP ALQTSSPYKQ AGPSPKTRAR QDSQGEEAEP   1350
pj01304s1   AFASPRELLL DHQAVFSQCP ALQTSSPYKQ AGPSPKTRAR QDSQGEEAEP   1103
Consensus   AFASPRELLL DHQAVFSQCP ALQTSSPYKQ AGPSPKTRAR QDSQGEEAEP   1350

pj01304GS   LPASPEAPAH SPKAKAADPP DGFCSSASTL EGLSVSDETC LSTSEPSARV   1400
pj01304s1   LPASPEAPAH SPKAKAADPP DGFCSSASTL EGLSVSDETC LSTSEPSARV   1153
Consensus   LPASPEAPAH SPKAKAADPP DGFCSSASTL EGLSVSDETC LSTSEPSARV   1400

pj01304GS   PDSVGVSPDD LDDTGQPVLE RGQLNGKRDT LWLALRETVY DPSLPASHHS   1450
pj01304s1   PDSVGVSPDD LDDTGQPVLE RGQLNGKRDT LWLALRETVY DPSLPASHHS   1203
Consensus   PDSVGVSPDD LDDTGQPVLE RGQLNGKRDT LWLALRETVY DPSLPASHHS   1450

pj01304GS   SLSWKGRGGP GDGSPVVLPN SQPDLPDVWL RRPSTHTSGY SS           1492
pj01304s1   SLSWKGRGGP GDGSPVVLPN SQPDLPDVWL RRPSTHTSGY SS           1245
Consensus   SLSWKGRGGP GDGSPVVLPN SQPDLPDVWL RRPSTHTSGY SS           1492
```

INDUSTRIAL APPLICABILITY

In view of the above knowledge and information, it is considered that the present DNA is a cancer-associated gene, and that it is possible to inhibit cancer by blocking the binding of the present protein to its ligand.

Accordingly, the present antibody is used not only in the detection of the present protein, but also as an agent for the treatment or prevention of cancers such as prostatic adenocarcinoma and ovarian carcinoma

What is claimed:

1. An isolated protein comprising the amino acid sequence of SEQ ID NO: 18.

2. An isolated recombinant protein which is obtained by the expression of a gene comprising:

(A) a nucleotide sequence encoding a polypeptide consisting of the amino acid sequence of SEQ ID NO: 18; or (B) a nucleotide sequence consisting of SEQ ID NO: 1 or (C) a nucleotide sequence consisting of nucleotides 561-4295 of SEQ ID NO: 1.

3. The isolated recombinant protein of claim 2, wherein the expressed gene comprises the nucleotide sequence encoding the polypeptide consisting of the amino acid sequence of SEQ ID NO: 18.

4. The isolated recombinant protein of claim 2, wherein the expressed gene comprises the nucleotide sequence consisting of SEQ ID NO: 1.

5. The isolated recombinant protein of claim 2, wherein the expressed gene comprises the nucleotide sequence consisting of nucleotides 561-4295 of SEQ ID NO: 1.

* * * * *